US011708336B2

(12) United States Patent
Rogers

(10) Patent No.: US 11,708,336 B2
(45) Date of Patent: Jul. 25, 2023

(54) ANODIC OXIDATION OF 5-AMINOURACIL

(71) Applicant: MediBeacon Inc., St. Louis, MO (US)

(72) Inventor: Thomas E. Rogers, Ballwin, MO (US)

(73) Assignee: MediBeacon Inc., St. Louis, MO (US)

( * ) Notice: Subject to any disclaimer, the term of this patent is extended or adjusted under 35 U.S.C. 154(b) by 294 days.

(21) Appl. No.: 17/066,702

(22) Filed: Oct. 9, 2020

(65) Prior Publication Data

US 2021/0107881 A1 Apr. 15, 2021
US 2022/0002254 A9 Jan. 6, 2022

Related U.S. Application Data

(60) Provisional application No. 62/913,196, filed on Oct. 10, 2019.

(51) Int. Cl.
*C07D 487/14* (2006.01)
*C07D 241/28* (2006.01)

(52) U.S. Cl.
CPC ......... *C07D 241/28* (2013.01); *C07D 487/14* (2013.01)

(58) Field of Classification Search
CPC .................................................. C07D 487/14
See application file for complete search history.

(56) References Cited

U.S. PATENT DOCUMENTS

| | | | |
|---|---|---|---|
| 6,600,042 | B1 | 7/2003 | Eichenberger et al. |
| 2003/0236452 | A1 | 12/2003 | Melker et al. |
| 2006/0095102 | A1 | 5/2006 | Perez |
| 2007/0021450 | A1 | 1/2007 | Sklarz et al. |
| 2008/0281173 | A1 | 11/2008 | Esenaliev et al. |
| 2013/0116512 | A1 | 5/2013 | Imran |
| 2015/0306486 | A1 | 10/2015 | Logan et al. |
| 2017/0298030 | A9 | 10/2017 | Rajagopalan et al. |
| 2018/0010881 | A1 | 1/2018 | Garst et al. |

OTHER PUBLICATIONS

Shirai. Journal of Heterocyclic Chemistry, 2000, 37, 1151-1156 (Year: 2000).*
Jiang et al., "Use of Electrochemistry in the Synthesis of Heterocyclic Structures", Chemical Reviews, 2018, vol. 118, pp. 4485-4540.
Shirai et al., "Syntheses and Fluorescent Properties of 2,5-Diamino-3,6-dicyanopyrazine Dyes", Dyes and Pigments, 1998, vol. 39, No. 1, pp. 49-68.
International Search Report and Written Opinion, PCT/US2020/54931, dated Jan. 29, 2021, 13 pages.
Baraldi et al., "Design, Synthesis, and Biological Activity of Hybrid Compounds between Uramustine and DNA Minor Groove Binder Distamycin A", J. Med. Chem., 2002, vol. 45, No. 17, pp. 3630-3638.
Baudisch et al., "The Oxidation of 5-Aminouracil", J. Biol. Chem., 1927, vol. 71, pp. 497-499.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine and Urea Clearances In Newborn Infants," J. Physiol., vol. 106, (1947), pp. 431-439.
Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.
Friedman et al., "A comparison of the renal clearances of allantoin and inulin in man," Fed. Proc., vol. 7, No. 1 Pt 1, (1948), 1 page.
Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.
Kaminsky et al., Some Congeners and Analogs of Dipyridamole, J. Med. Chem., 1966, vol. 9, pp. 610-612.
Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.
Nagpal et al., "Combined Fluorescein, Indocyanine angiography and Optical Coherent Tomography Using Spectralis," Rajasthan Journal of Ophthalmology, (2011), 8 pages.
Navar et al., "Distal Tubular Feedback in the Autoregulation of Single Nephron Glomerular Filtration Rate," J. Clin. Invest., vol. 53, (1974), pp. 516-525.
Nicholson et al., "Renal Function as Affected by Experimental Unilateral Kidney Lesions: I. Nephrosis Due to odium Rartrate," J. Exp. Med., vol. 68, (1938), pp. 439-456.
Pill et al., "Fluorescein-labeled Sinistrin as Marker of Glomerular Filtration Rate," European Journal of Medicinal Chemistry, vol. 40, (2005), pp. 1056-1061.
Poujeol et al., "Glomerular Filtration Rate and Microsphere Distributions in Single Nephron of Rat Kidney," Pflugers Arch., vol. 357, (1975), pp. 291-301.
Robson et al., "The Determination of the Renal Clearance of Inulin in Man," Q. J. Exp. Physiol., vol. 35, (1949), pp. 111-134.
Schock-Kusch et al., "Transcutaneous measurement of glomerular filtration rate using FITC-sinistrin in rats," Nephrol Dial Transplant, vol. 24, (2009), pp. 2997-3001.

(Continued)

*Primary Examiner* — Noble E Jarrell
(74) *Attorney, Agent, or Firm* — Armstrong Teasdale LLP

(57) ABSTRACT

A process for preparing pyrimido[4,5-g]pteridine-2,4,7,9-tetraol, or a salt thereof, is provided. A process for the preparation of 3,6-diaminopyrazine-2,5-dicarboxylic acid, or a salt thereof, from pyrimido[4,5-g]pteridine-2,4,7,9-tetraol, or a salt thereof, is further provided. A process for preparing a substituted pteridine compound, or a salt thereof, is further provided. A process for the preparation of a N-substituted 3,6-diaminopyrazine-2,5-dicarboxylic acid from a substituted pteridine compound, or a salt thereof, is further provided.

14 Claims, 6 Drawing Sheets

(56) References Cited

OTHER PUBLICATIONS

Shannon et al., "The Renal Excretion of Inulin and Creatinine by the Anaesthetized Dog and the Pump-Lung-Kidney Preparation", J. Physiol., vol. 98, (1940), pp. 97-108.
Taylor et al., Pyrimidopteridines by Oxidative Self-condensation of Aminopyrindines, J. Am. Chem. Soc., 1955, vol. 77, No. 8, pp. 2243-2248.
Yu et al., "Rapid determination of renal filtration function using an optical ratiometric imaging approach," Am J. Physiol. Renal. Physiol., vol. 292, (2007), pp F1873-F18.
International Search Report received for PCT Patent Application No. PCT/US2019/013784, dated May 7, 2019, 6 pages.
International Preliminary Report on Patentability received for PCT Patent Application No. PCT/US2019/013784, dated Jul. 30, 2020, 8 pages.

\* cited by examiner

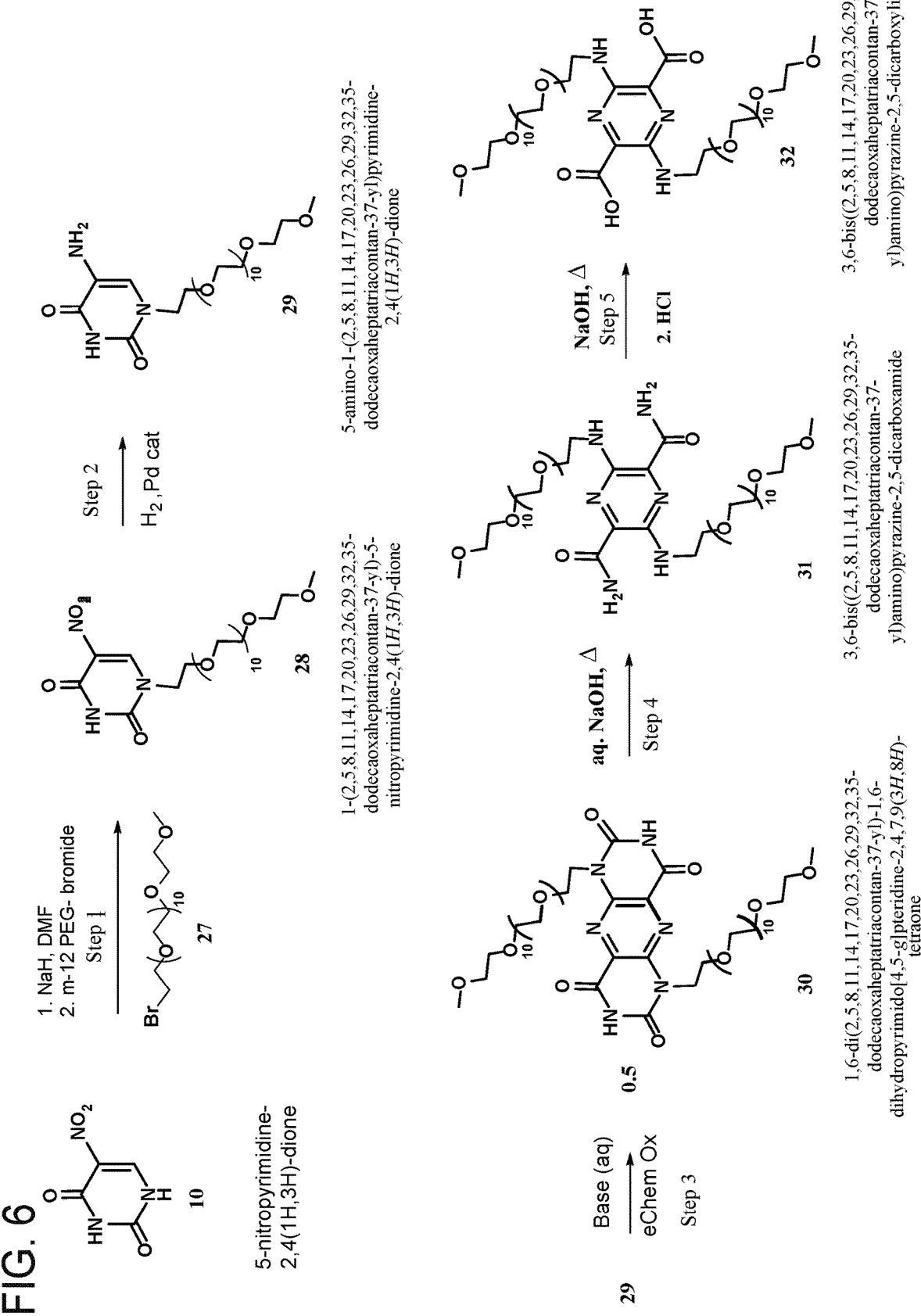

ANODIC OXIDATION OF 5-AMINOURACIL

CROSS REFERENCE TO RELATED APPLICATION

This application claims priority to U.S. Provisional Application No. 62/913,196 filed Oct. 10, 2019, the contents of which are incorporated in their entirety.

BACKGROUND OF THE DISCLOSURE

The field of the disclosure relates generally to anodic oxidation chemistry.

More particularly, the disclosure relates to the anodic oxidation of 5-aminouracil to form potassium 4,9-dihydroxypyrimido[4,5-g]pteridine-2,7-bis(olate) that may then be hydrolyzed to form 3,6-diaminopyrazine-2,5-dicarboxylic acid. 3,6-diaminopyrazine-2,5-dicarboxylic acid is an intermediate used in the preparation of higher value products, such as imaging agents.

Methods for the preparation of potassium 4,9-dihydroxypyrimido[4,5-g]pteridine-2,7-bis(olate) and 3,6-diaminopyrazine-2,5-dicarboxylic are known in the art. Problematically, the prior art methods use toxic and environmentally hazardous materials.

A need therefore exists for new processes for preparing potassium 4,9-dihydroxypyrimido[4,5-g]pteridine-2,7-bis(olate) and 3,6-diaminopyrazine-2,5-dicarboxylic that reduce environmental burden and reduce industrial hygiene issues.

BRIEF DESCRIPTION

In some aspects of the disclosure, a process for preparing divalent salts of pyrimido[4,5-g]pteridine-2,4,7,9-tetraol (Compound 2a) is provided. The process comprises step 1a directed to anodic oxidation of 5-aminopyrimidine-2,4(1H,3H)-dione (Compound 1), in the presence of an aqueous base to form pyrimido[4,5-g]pteridine-2,4,7,9-tetraol (Compound 2a) followed by step 1b directed to treatment of Compound 2a with a base to form Compound 2 as follows:

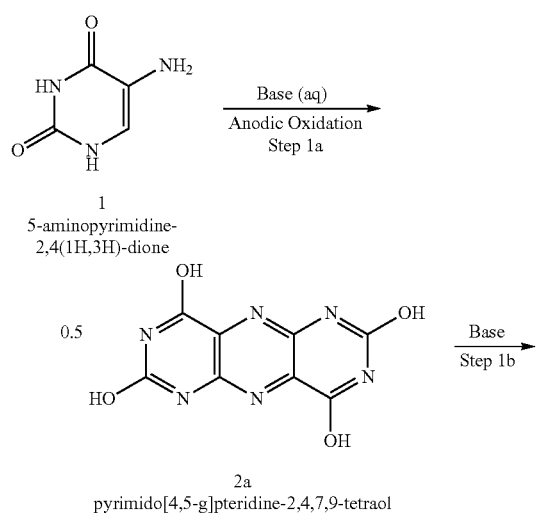

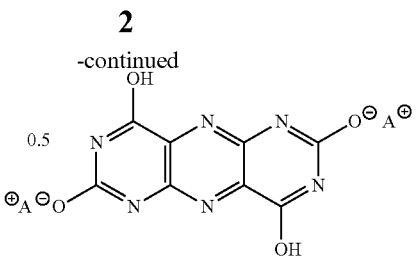

where A+ is a monovalent cation.

In some aspects of the disclosure, a process for preparing a substituted pteridine compound, or a salt thereof, is provided. The process comprises step 1a directed to anodic oxidation of compound 7 in the presence of a base and a solvent to form compound 8 as follows;

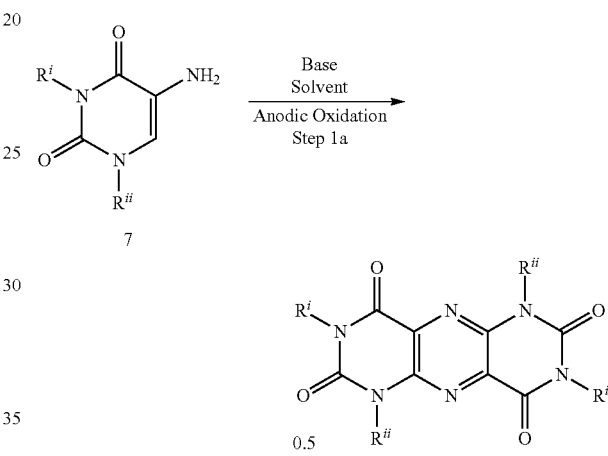

$R^i$ and $R^{ii}$ are independently selected from: optionally substituted alkyl; optionally substituted cycloalkyl; optionally substituted aryl; optionally substituted alkoxy; optionally substituted —C(O)-alkyl; optionally substituted amino; optionally substituted polyol ethers and optionally substituted polyethers; a polypeptide chain (AA); and polysaccharide chain (PS).

BRIEF DESCRIPTION OF THE DRAWINGS

FIG. 1 further depicts a process of the present disclosure for preparing (2R,2'R)-2,2'-((3,6-diaminopyrazine-2,5-dicarbonyl)bis(azanediyl))bis(3-hydroxypropanoic acid) from 3,6-diaminopyrazine-2,5-dicarboxylic acid.

FIG. 2 further depicts a prior art process for preparing (2R,2'R)-2,2'-((3,6-diaminopyrazine-2,5-dicarbonyl)bis(azanediyl))bis(3-hydroxypropanoic acid) from 3,6-diaminopyrazine-2,5-dicarboxylic acid.

FIG. 6 depicts a proposed process for preparing a substituted pyrazine-2,5-dicarboxylic acid.

DETAILED DESCRIPTION

Figure 1:
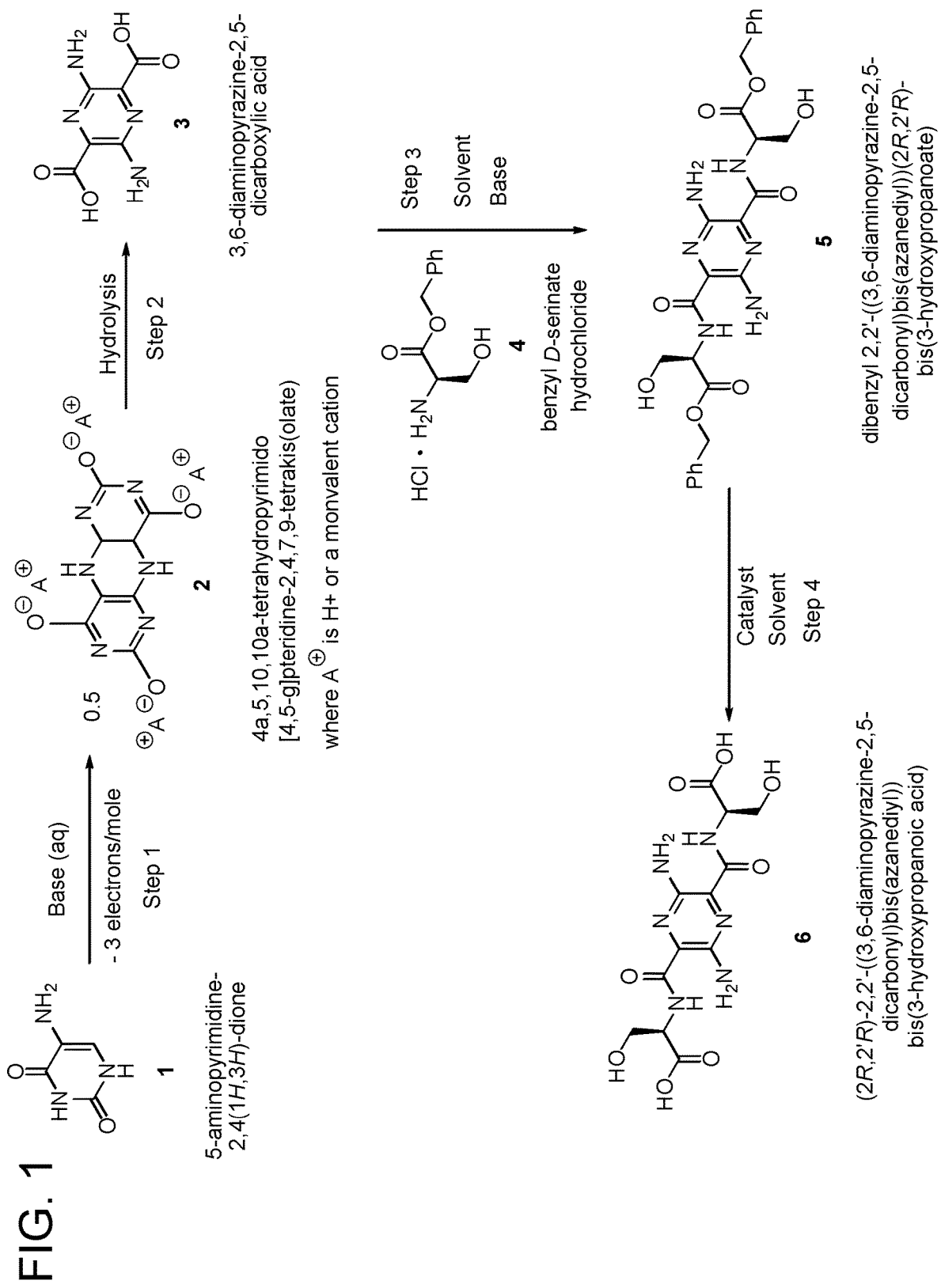
FIG. 1 depicts a process for preparing 3,6-diaminopyrazine-2,5-dicarboxylic acid according to the present disclosure.

The present disclosure is generally directed an improved process for the preparation of salts of pyrimido[4,5-g]pteridine-2,4,7,9-tetraol (Compound 2) by anodic oxidation of 5-aminouracil (5-aminopyrimidine-2,4(1H,3H)-dione) (Compound 1). In some aspects, Compound 2 may be converted by basic hydrolysis to form 3,6-diaminopyrazine-2,5-dicarboxylic acid (Compound 3), that is useful as an intermediate for the preparation of higher values products. In some such aspects, Compound 3 is used as an intermediate in the preparation of medical imaging agents. One such imaging agent is 3,6-diaminopyrazine-2,5-dicarboxylic acid that is useful as a fluorescent dye, for instance and without limitation, for evaluating renal function and for imaging vasculature, such as eye vasculature. A process of the present disclosure for preparing Compound 3 is depicted in FIG. 1 as steps 1 and 2. One particular aspect of the present disclosure directed to a process for preparing (2R,2'R)-2,2'-((3,6-diaminopyrazine-2,5-dicarbonyl)bis(azanediyl))bis(3-hydroxypropanoic acid) (Compound 6), from Compound 3 is depicted in FIG. 1 as steps 3 and 4.

Figure 2:
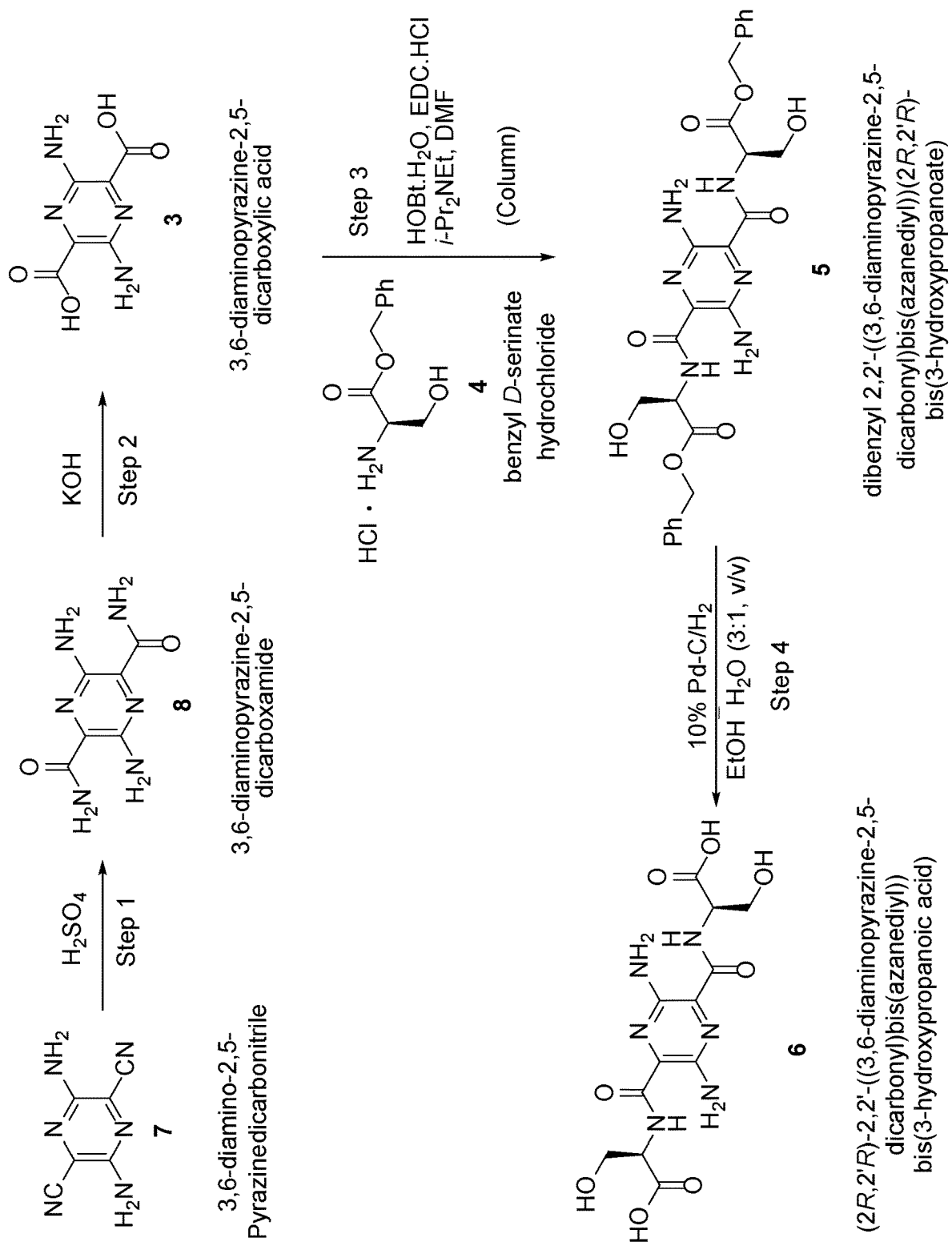
FIG. 2 depicts a first prior art process for preparing 3,6-diaminopyrazine-2,5-dicarboxylic acid.

One prior art process for preparing 3,6-diaminopyrazine-2,5-dicarboxylic acid is depicted in FIG. 2 as steps 1 and 2. In step 1, 3,6-diamino-2,5-pyrazinedicarbonitrile (Compound 7) is contacted with sulfuric acid to form 3,6-diaminopyrazine-2,5-dicarboxamide (Compound 8). Problematically, this prior art process starts with Compound 7 that is typically prepared by a complex process and environmentally dangerous process, such as taught in U.S. Pat. No. 5,294,711. US '711 teaches that diphenyldisulfide is reacted with hydrogen cyanide in an organic solvent (e.g., di-methoxyethane, acetonitrile, xylene, chloroform, methanol or benzene) to form 2,3-diamino-3-(phenylthio)acrylonitrile ("DAAN"), where DAAN is thereafter converted to Compound 7 by contact with citric acid. In FIG. 2, step 2, Compound 8 is contacted with KOH to form 3,6-diamino-pyrazine-2,5-dicarboxylic acid (Compound 3). FIG. 2 further depicts a prior art process for preparing dibenzyl 2,2'-((3,6-diaminopyrazine-2,5-dicarbonyl)bis(azanediyl)) (2R,2'R)-bis(3-hydroxypropanoate) (Compound 5) by contacting Compound 3 with benzyl D-serinate hydrochloride (Compound 4) in dimethylformamide ("DMF") solvent in the presence of hydroxybenzotriazole ("HOBt", a racemization inhibitor), 1-ethyl-3-(3-imethylaminopropyl)carbo-diimide ("EDC", a carboxyl activating agent), and N,N-diisopropylethylamine ("i-PrNEt", a base). FIG. 2 further depicts a prior art process for preparing Compound 6 by contacting Compound 5 with a palladium catalyst in an ethanol/water solvent.

Figure 3:
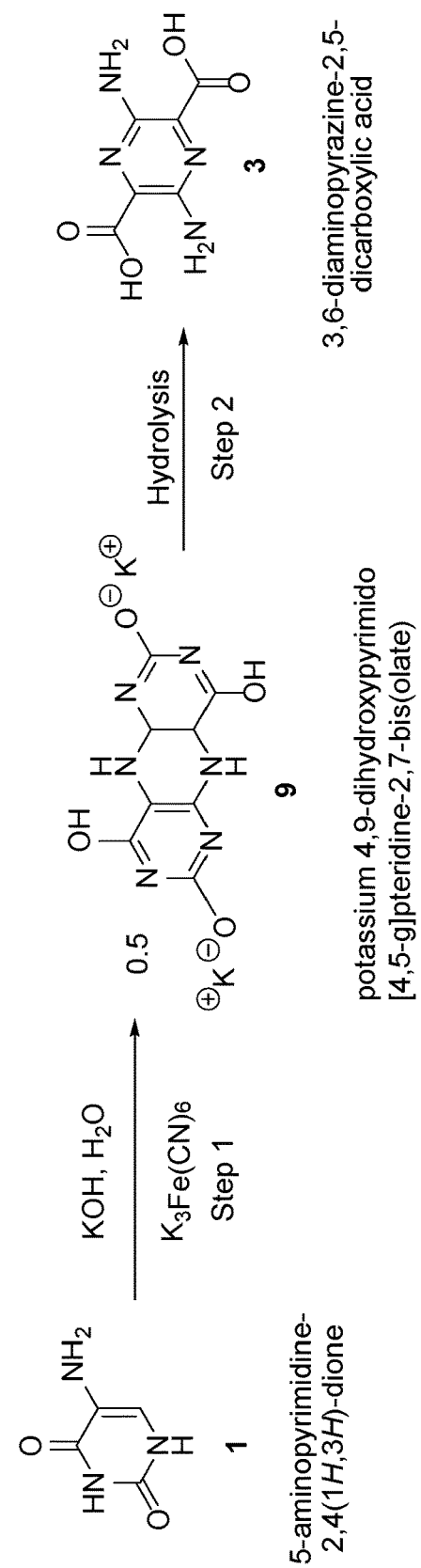
FIG. 3 depicts a second prior art process for preparing 3,6-diaminopyrazine-2,5-dicarboxylic acid.

Another prior art process for preparing 3,6-diaminopyrazine-2,5-dicarboxylic acid is depicted in FIG. 3 as Steps 1 and 2. In Step 1, Compound 1 is contacted with potassium ferrocyanide ($K_3Fe(CN)_6$) in aqueous KOH to form potassium 4,9-dihydroxypyrimido[4,5-g]pteridine-2,7-bis(olate) (Compound 9). In Step 2, Compound 9 is converted by basic hydrolysis to Compound 3. Problematically, potassium ferrocyanide is an irritant to personnel, can release toxic hydrogen cyanide upon contact with acid, and is classified as an environmental hazard due to harmful effects on aquatic life. The prior art process of FIG. 3 is taught, for instance, by Oskar Baudisch, et al., *The Oxidation of 5-Aminouracil*, J. Biol. Chem., 71:497-499 (1927), by E. C. Taylor, et al., *Pyrimidopteridines by Oxidative Self-condensation of Aminopyrindines*, J. Am. Chem. Soc., 77, (8), 2243-2247 (1955), and by D. Kaminsky, et al., *Some Congeners and Analogs of Dipyridamole*, J. Med. Chem., 9, 610 (1966).

The Applicant has discovered an anodic oxidation process for preparing pyrimido[4,5-g]pteridine-2,4,7,9-tetraol (Compound 2a), and salts thereof, that is environmentally benign and avoids the use of toxic and hazardous reactants. The reaction is depicted as steps 1a and 1b in FIG. 1 and is generally directed to anodic oxidation of Compound 1 in the presence of an aqueous base to form Compound 2a followed by formation of Compound 2 by further treatment with as base as follows:

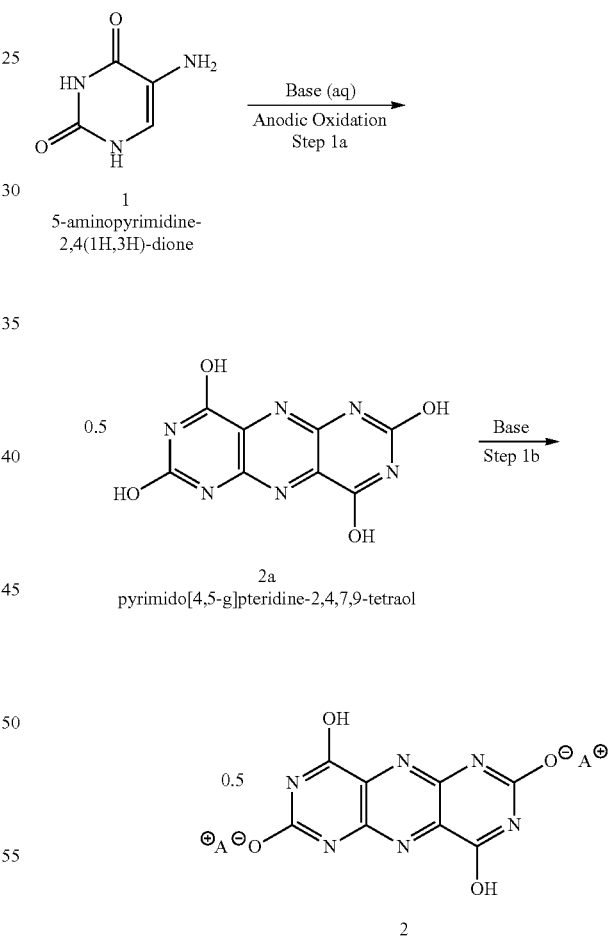

where $A^+$ is $H^+$ or a monovalent cation. The yield of compound 2 based on compound 1 is at least 20%, at least 30%, or at least 40%, such as for instance 20%, 25%, 30%, 35% or 40%.

Under one theory, and without being bound to any particular theory, it is believed that the step 1 reaction mechanism is as follows, where the base KOH is illustrated:

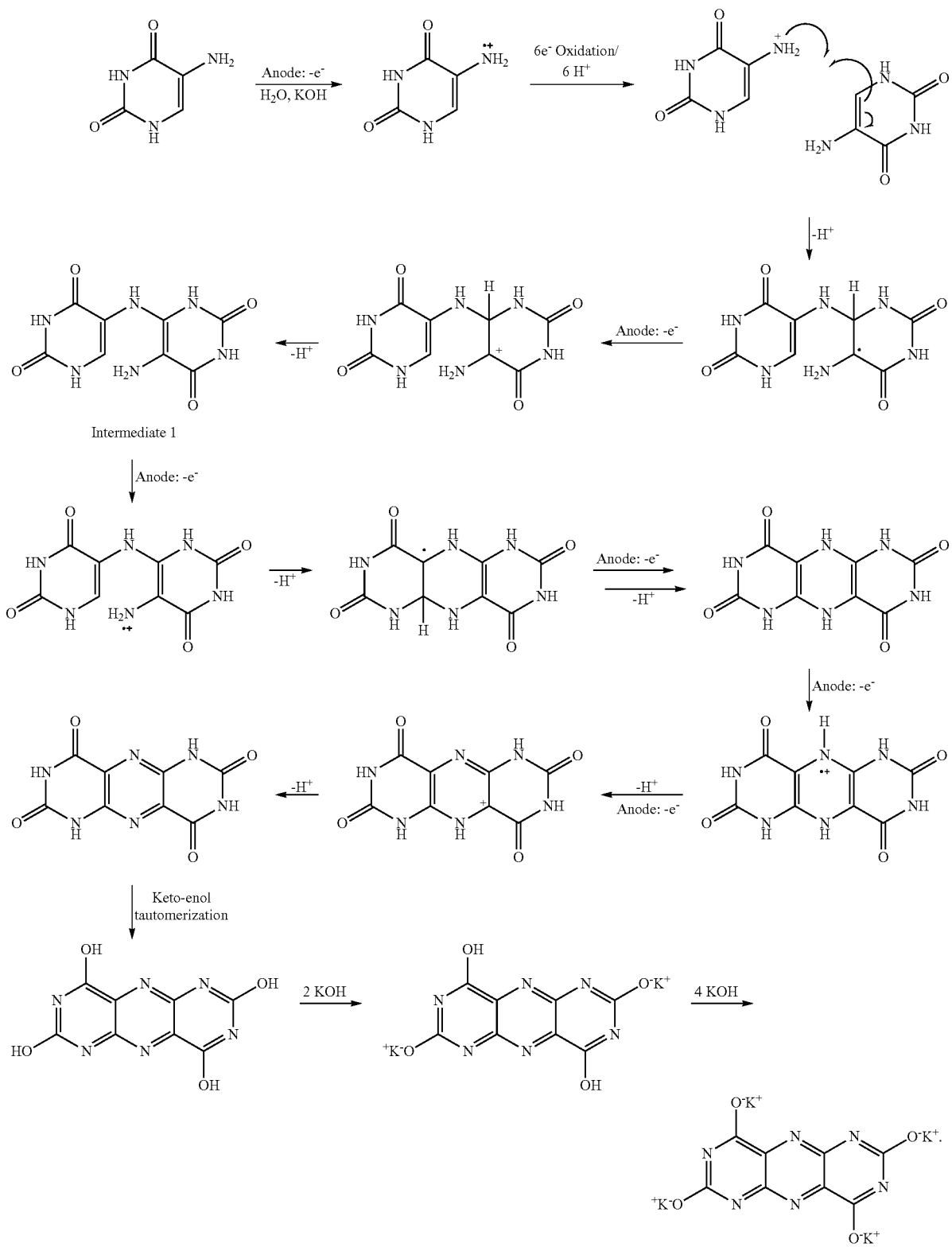

The number of A⁺ cations (e.g., K⁺) relates to the stoichiometry of base to the free acid. The salt form may be mono, di, tri, or tetra.

Bases within the scope of the present disclosure comprise a cation and an anion and include inorganic and organic bases. Inorganic bases include sodium, potassium, ammonium, calcium, magnesium, iron, zinc, copper, manganese, and aluminum salts. Non-limiting examples include phosphates such as dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate and triammonium phosphate; acetates such as potassium acetate, sodium acetate and ammonium acetate; formates such as potassium formate and sodium formate; carbonates such as potassium carbonate, sodium carbonate, potassium hydrogen carbonate and sodium hydrogen carbonate; and alkali metal hydroxides such as lithium hydroxide, sodium hydroxide, potassium hydroxide, rubidium hydroxide caesium hydroxide magnesium hydroxide, calcium hydroxide, manganese (II) hydroxide, iron hydroxide, cobalt hydroxide, nickel (II) hydroxide, copper (II) hydroxide, zinc hydroxide, and cadmium hydroxide. Organic bases are of the general formulae R-amine (e.g., $R_4N^+OH^-$) and $OR^-$ where R is an organic moiety such as alkyl, aryl, etc. Examples of organic bases include primary, secondary, and tertiary amines, substituted amines including naturally occurring substituted amines, and cyclic amines such as pyridine, isopropylamine, trimethylamine, diethylamine, triethylamine, triethanolamine, diisopropylamine, ethanolamine, 2-diethylaminoethanol, trimethylamine, di cyclohexylamine, ethylenediamine, purines, piperazine, piperidine, N-ethylpiperidine, and alkali metal alkoxides (e.g., sodium methoxide). In some aspects, the base is a strong base, such as alkali metal hydroxide base. Non-limiting examples of suitable bases include sodium hydroxide and potassium hydroxide.

In some aspects, the solvent is a polar solvent. In some aspects, the solvent is a polar protic solvent. Non-limiting examples of suitable polar protic solvents include water, methanol, ethanol, n-propanol, i-propanol, n-butanol, acetic acid, and combinations thereof. In some aspects, the solvent is water. In some aspects, the solvent is a polar solvent. In some aspects, the solvent is a polar protic solvent. Non-limiting examples of suitable polar protic solvents include water, methanol, ethanol, n-propanol, i-propanol, n-butanol, acetic acid, and combinations thereof. In some aspects, the solvent is water. In some aspects, compound 2 is the potassium salt of Compound 2a as follows:

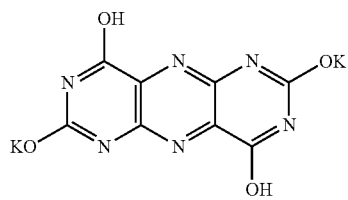

potassium 4,9-dihydroxypyrimido[4,5-g]pteridine-2,7-bis(olate).

Electrochemical cells known in the art are generally suitable for practicing the present disclosure, and may include divided or undivided cells. For instance, and without limitation, the electrochemical cell may be a divided flow cell. Divided flow cells generally comprise two parallel rectangular electrode plates separated by a membrane placed generally equidistantly from each electrode. The electrode package is typically housed in a chemically stable, non-conductor, (e.g. polypropylene) constructed to both house the electrodes and separating membrane thereby allowing for separate generally uniform solvent flow over both electrodes. Solvent flow may be produced a recirculating pumping system where anolyte and catholyte are circulated through their respective compartments. Heat exchangers may be optionally incorporated to keep the reaction temperature within certain set boundaries.

In other configurations an undivided cell may be employed where the membrane or porous barrier is removed and electrolytic solution allowed to freely pass between both electrodes.

In some aspects, an indirect electrochemical system could be used. For instance, and without limitation, a complex of iron(II) could be anodically transformed into iron (III) at high current efficiency and extent (>90%). The anodic solution containing Fe(III) could react with Compound 1 to produce Compound 2, or a salt thereof.

In another aspect, an electrochemical catalytic system may be employed where, for instance, and without limitation, a complex of iron(II) could be anodically transformed into iron(III) in the presence of Compound 2 to produce Compound 2, or a salt thereof, regenerating Fe(II) that would be available to be re-oxidized at the anode to produce more Fe(III). Thus, the reaction would be catalytic in Fe(II).

In some aspects, Compound 2, may by hydrolyzed in an aqueous base to form Compound 3 as depicted in step 2 of FIG. 1. The reaction scheme is as follows, where $A^+$ is $H^+$ or a monovalent cation:

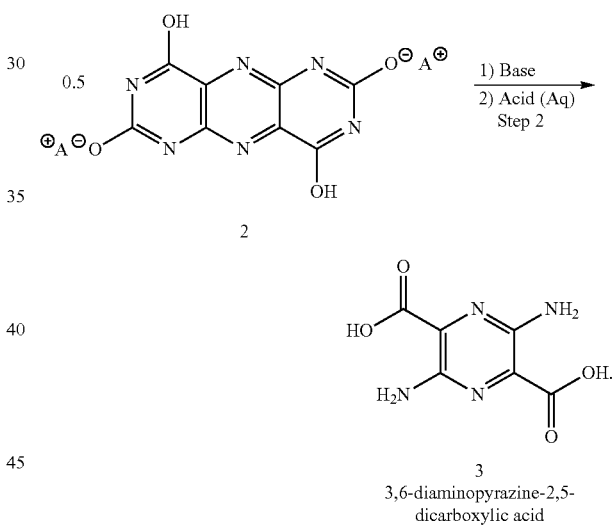

3
3,6-diaminopyrazine-2,5-dicarboxylic acid

In some such aspects Compound 2 is potassium 4,9-dihydroxypyrimido[4,5-g]pteridine-2,7-bis(olate). In some aspects, the base is a strong base, such as NaOH or KOH. The hydrolysis step produces Compound 3 in aqueous solution as a salt of the base cation. In some further aspects, after the hydrolysis step, an acid is added to the solution to precipitate Compound 3 (di-acid) from aqueous solution and form a slurry. In some aspects, the acid is a strong acid, such as for example and without limitation, HCl. Solid Compound 3 may be isolated from the slurry by methods known in the art, such as filtration or centrifugation. Isolated Compound 3 may be optionally further purified by washing and optionally dried.

In some aspects, Compound 3 may be reacted with NHR, acid salt (Compound 4) in a solvent to form the corresponding amide, Compound 5, as depicted in step 3 of FIG. 1. The reaction scheme is as follows:

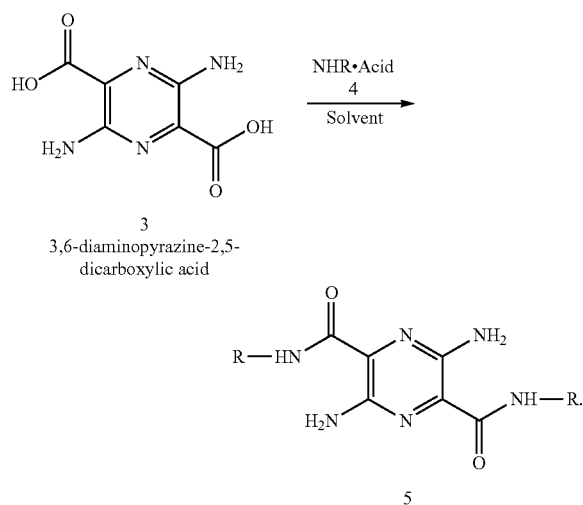

3
3,6-diaminopyrazine-2,5-dicarboxylic acid

5

General methods of forming amides by coupling a compound having an amine substituent (e.g., compound 4) and a compound having a carboxyl substituent (e.g., compound 3) are known to those skilled in the art. In particular, US 2018/0010881 (incorporated by reference herein in its entirety) discloses forming compound the compound 3,6-diamino-$N^2,N^5$-bis(D-serine)-pyrazine-2,5-dicarboxamide as follows. In step 1, 3,6-diamino-$N^2,N^5$-bis(O-benzyl-(D)-serine methyl ester)-pyrazine-2,5-dicarboxamide was formed as follows. A mixture of sodium 3,6-diaminopyrazine-2,5-dicarboxylate (300 mg, 1.24 mmol), (D)-Ser(OBn)-OMe-HCl salt (647 mg, 2.64 mmol), HOBt-H2O (570 mg, 3.72 mmol) and EDC-HCl (690 mg, 3.60 mmol) in DMF (25 mL) was treated with TEA (2 mL). The resulting mixture was stirred for 16 h and concentrated. The mixture was concentrated to dryness and the residue was partitioned with EtOAc and water. The layers were separated and the EtOAc solution was washed with saturated NaHCO$_3$ and brine. The solution was dried over anhydrous Na$_2$SO$_4$, filtered and concentrated, which afforded 370 mg (51% yield) of the bisamide as a bright yellow powder: $^1$NMR (300 MHz, CDCl3) δ 8.47 (d, J=8.74 Hz, 2H), 7.25-7.37 (complex m, 10H), 5.98 (bs, 4H), 4.85 (dt, J=8.7, 3.3 Hz, 2H), 4.56 (ABq, J=12.6, Hz, Av=11.9 Hz, 4H), 3.99 (one half of an ABq of d, J=8.7, 3.3, Av obscured, 2H), 3.76-3.80 (one half of an ABq-obscured, 2H), 3.78 (s, 6H). $^{13}$C NMR (75 MHz, CDCl3) δ 170.5 (s), 165.1 (s), 146.8 (s), 138.7 (s) 128.6 (d), 128.1 (d), 127.8 (d), 126.9 (s), 73.5 (t), 69.8 (t), 53.0 (q), 52.9 (q). LCMS (5-95% gradient acetonitrile with 0.1% TFA over 10 min), single peak retention time=4.93 min on 30 mm column, (M+H)$^+$=581. In step 2, 3,6-diamino-$N^2,N^5$-bis(O-benzyl-(D)-serine)-pyrazine-2,5-dicarboxamide was formed as follows. The product from Step 1 (370 mg, 0.64 mmol) in THF (10 mL) was treated with 1.0 N sodium hydroxide (2.5 mL). After stirring at room temperature for 30 min, the reaction was judged complete by TLC. The pH was adjusted to approximately 2 by the addition of 1.0 N HCl and the resulting solution was extracted (3×) with EtOAc. The layers were combined, dried over sodium sulfate, filtered and concentrated to afford 353 mg (100% yield) of the di-acid as an orange foam: LCMS (5-95% gradient acetonitrile in 0.1% TFA over 10 min), retention time=4.41 min on 30 mm column, (M+H)$^+$=553. In step 3, 3,6-diamino-$N^2,N^5$-bis(D-serine)-pyrazine-2,5-dicarboxamide was formed as follows. To the product from Step 2 (353 mg, 0.64 mmol) in methanol (20 mL) was added 5% Pd/C (300 mg) and ammonium formate (600 mg). The resulting reaction was heated at reflux for 2 h. The reaction was cooled to room temperature, filtered through a plug of celite and concentrated. The residue was recrystallized from methanol-ether to provide 191 mg (80% yield) of title compound Example 2 as a yellow foam: $^1$NMR (300 MHz, DMSO-d6) δ 8.48 (d, J=6.9 Hz, 2H), 6.72 (bs, 4H), 3.95 (apparent quartet, J=5.1 Hz, 2H), 3.60 (apparent ABq of doublets; down-field group centered at 3.71, J=9.9, 5.1 Hz, 2H; up-field group centered at 3.48, J=20 9.9, 6.3 Hz, 2H). $^{13}$C NMR (75 MHz, CDCl3) δ 172.9 (s), 164.9 (s), 147.0 (s), 127.0 (s), 62.9 (d), 55.7 (t). LCMS (5-95% gradient acetonitrile in 0.1% TFA over 10 min), single peak retention time=1.45 min on 30 mm column, (M+H)$^+$=373. UV/vis (100 μM in PBS) λabs=434 nm. Fluorescence λex=449 nm, λem=559 nm.

Those skilled in the art would recognize that 3,6-diaminopyrazine-2,5-dicarboxylate could be reacted with amines other than (D)-Ser(OBn)-OMe-HCl salt to form an amide of the structure of compound 6. For instance, US 2018/0010881 further provides examples for formation of amides where the (D)-Ser(OBn)-OMe-HCl salt amine is replaced with (L)-Ser(OBn)-OMe-HCl, is replaced with bis-2-(methoxyethyl) amine, is replaced with racemic (2,2-dimethyl-1,3-dioxolan-4-yl)methanamine, is replaced with tert-butyl 2-aminoethylcarbamate, is replaced with Asp(OBn)-OMe-p-TosH salt, is replaced with 2-OBn-β-serine-OMe-HCl salt, is replaced with m-dPEG24-amine, is replaced with benzyl 3-aminopropanoate p-toluene sulfonate, is replaced with ethyl 4-amino-butyrate HCl salt, is replaced with 3-amino-5-oxo-furane HCl salt, is replaced with 3-dimethyl-beta-alanine ethyl ester HCl salt, is replaced with ethyl 3-(3-pyridyl)-propanoate HCl salt, and is replaced with methyl-2-O-benzyl-3-amino-propionate HCl salt.

In some aspects, the solvent is a polar solvent. In some aspects, the solvent is a polar aprotic solvent. Non-limiting examples of suitable solvents include tetrahydrofuran, DMF, ethyl acetate, and acetonitrile, and combinations thereof. In some aspects, the solvent is DMF.

The step 3 reaction mixture may further comprise a racemization inhibitor, for instance and without limitation, HOBt, 7-aza-1-hydroxybenzotriazole, ethyl 2-cyano-2-(hydroxyimino)acetate, N-hydroxysuccinimide, or hydroxy-3,4-dihydro-4-oxo-1,2,3-benzotriazine. The step 3 reaction mixture may further comprise a coupling agent (such as a carboxyl group activator), for instance and without limitation, EDC or N,N'-dicyclohexylcarbodiimide. The step 3 reaction mixture may further comprise a base, for instance and without limitation, an organic amine base such as i-PrNEt or N-methylmorpholine.

In some aspects NHR, acid salt, is a polypeptide chain that includes one or more natural or unnatural α-amino acids linked together by peptide bonds. The polypeptide chain (AA) may be a homopolypeptide chain or a heteropolypeptide chain, and may be any appropriate length. For instance, in some embodiments, the polypeptide chain may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the α-amino acids of the polypeptide chain (AA) are selected from aspartic acid, asparigine, arginine, histidine, lysine, glutamic acid, glutamine, serine, and homoserine. In some embodiments, the α-amino acids of the polypeptide chain (AA) are selected from aspartic acid, glutamic acid, serine, and homoserine. In some embodiments, the polypeptide chain (AA) refers to a single amino acid (e.g., aspartic acid or serine). In some embodiments the amino acid is D-serine.

In some aspects, NHR, acid salt, is $NHR^1R^2$.

In such aspects, each $R^1$ is independently $—(CH_2)_a(CH_2CH_2O)_b(CH_2)_cNR^{10}CONR^{11}(CH_2)_d(CH_2CH_2O)_eR^{20}$, $—(CH_2)_a(CH_2CH_2O)_b(CH_2)_cNR^{12}CSNR^{13}(CH_2)_d(CH_2CH_2O)_eR^{21}$, $—(CH_2)_a(CH_2CH_2O)_b(CH_2)_cCONR^{14}(CH_2)_d(CH_2CH_2O)_eR^{22}$, $—(CH_2)_a(CH_2CH_2O)_b(CH_2)_cNR^{15}SO_2$ $(CH_2)_d(CH_2CH_2O)_eR^{23}$, $—(CH_2)_a(CH_2CH_2O)_b(CH_2)_cSO_2NR^{16}(CH_2)_d(CH_2CH_2O)_eR^{24}$, $—(CH_2)_a(CH_2CH_2O)_b(CH_2)_cNR^{17}CO(CH_2)_d(CH_2CH_2O)_eR^{25}$, $—(CH_2)_a(CH_2CH_2O)_b(CH_2)_cNR^{18}CO_2(CH_2)_d(CH_2CH_2O)_e$ $R^{26}$, or $—(CH_2)_a(CH_2CH_2O)_b(CH_2)_cOC(O)NR^{19}CO_2$ $(CH_2)_d(CH_2CH_2O)_eR^{27}$; $—(CH_2)_eOR^{68}$, $—CH_2(CHOH)_cR^{69}$, $—CH_2(CHOH)_cCO_2H$, $—(CHCO_2H)_cCO_2H$, $—(CH_2)_cNR^{70}R^{71}$; $—CH[(CH_2)_fNH_2]_cCO_2H$, $—CH[(CH_2)_f\ NH_2]_cCH_2OH$, $—CH_2(CHNH_2)_cCH_2NR^{72}R^{73}$, $—(CH_2CH_2O)_eR^{74}$, $—(CH_2)_cCO(CH_2CH_2O)_eR^{75}$, $—(CH_2)_u(CH_2CH_2O)_j(CH_2)_kNR^{58}C(O)NR^{59}(CH_2)_l(CH_2CH_2O)_oR^{76}$, $—(CH_2)_u(CH_2CH_2O)_j$ $(CH_2)_lNR^{60}C(S)NR^{61}(CH_2)_l(CH_2CH_2O)_oR^{77}$, $—(CH_2)_u(CH_2CH_2O)_j(CH_2)_kC(O)NR^{62}(CH_2)_l(CH_2CH_2O)_oR^{78}$, $—(CH_2)_u(CH_2CH_2O)_j(CH_2)_kS(O)_2NR^{63}(CH_2)_l(CH_2CH_2O)_oR^{79}$, $—(CH_2)_u(CH_2CH_2O)_j(CH_2)_lNR^{64}S(O)_2(CH_2)_l(CH_2CH_2O)_oR^{80}$, $—(CH_2)_u(CH_2CH_2O)_j(CH_2)_lNR^{65}C(O)(CH_2)_l(CH_2CH_2O)_oR^{81}$, $—(CH_2)_j(CH_2CH_2O)_j(CH_2)_kNR^{66}C(O)O(CH_2)_l(CH_2CH_2O)_oR^{82}$, or $—(CH_2)_j(CH_2CH_2O)_j(CH_2)_kOC(O)NR^{67}(CH_2)_l(CH_2CH_2O)_oR^{83}$, $—(CH_2)_aSO_3H$, $—(CH_2)_aSO_3^-$, $—(CH_2)_aOSO_3H$, $—(CH_2)_aOSO_3^-$, $—(CH_2)_aNHSO_3H$, $—(CH_2)_aNHSO_3^-$, $—(CH_2)_aPO_3H_2$, $—(CH_2)_aPO_3H^-$, $—(CH_2)_aPO_3^=$, $—(CH_2)_aOPO_3H_2$, $—(CH_2)_aOPO_3H^-$, or $—(CH_2)_aOPO^3$.

Each of $R^2$, $R^{10}$, $R^{11}$, $R^{12}$, $R^{13}$, $R^{14}$, $R^{15}$, $R^{16}$, $R^{17}$, $R^{18}$, $R^{19}$, $R^{58}$, $R^{59}$, $R^{60}$, $R^{61}$, $R^{62}$, $R^{63}$, $R^{64}$, $R^{65}$, $R^{66}$ and $R^{67}$ is independently —H or —$CH_3$.

Each of $R^{20}$, $R^{21}$, $R^{22}$, $R^{23}$, $R^{24}$, $R^{25}$, $R^{26}$, and $R^{27}$ is independently —H, —$CH_3$, $—(CH_2)_gNR^{28}C(O)NR^{29}(CH_2)_g$ $(CH_2CH_2O)_hR^{38}$, $—(CH_2)_gNR^{30}CSNR^{31}(CH_2)_g(CH_2CH_2O)_hR^{39}$, $—(CH_2)_gC(O)NR^{32}(CH_2)_g(CH_2CH_2O)_hR^{40}$, $—(CH_2)_gS(O)_2NR^{33}(CH_2)_g(CH_2CH_2O)_hR^{41}$, $—(CH_2)_fNR^{34}S(O)_2(CH_2)_g(CH_2CH_2O)_hR^{42}$, $—(CH_2)_fNR^{35}C(O)(CH_2)_g(CH_2CH_2O)_hR^{43}$, $—(CH_2)_fNR^{36}C(O)O(CH_2)_g(CH_2CH_2O)_hR^{44}$, $—(CH_2)_fOC(O)NR^{37}(CH_2)_g(CH_2CH_2O)_hR^{45}$, —CO(AA), or —CONH(PS).

Each of $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ is independently —H or —$CH_3$.

Each of $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, and $R^{80}$ is independently —H, —$CH_3$, $—(CH_2)_pS(O)_2NR^{84}(CH_2)_q(CH_2CH_2O)_sR^{81}$, $—(CH_2)_pNR^{85}S(O)_2(CH_2)_q(CH_2CH_2O)_sR^{83}$, $—(CH_2)_pNR^{86}C(O)(CH_2)_q(CH_2CH_2O)_sR^{85}$, $—(CH_2)_pNR^{86}C(O)O(CH_2)_q(CH_2CH_2O)_sR^{87}$, or $—(CH_2)_pOC(O)NR^{88}(CH_2)_q(CH_2CH_2O)_sR^{89}$.

Each of $R^{81}$, $R^{82}$, $R^{83}$, $R^{84}$, $R^{85}$, $R^{86}$, $R^{87}$, $R^{88}$, and $R^{89}$ is independently —H or —$CH_3$.

AA is as defined above.

Each (PS) is independently a sulfated or non-sulfated polysaccharide chain comprising one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose).

Each of t and u is independently 1, 2, 3, 4, or 5.

Each of a, d, g, l, and q is independently 0, 1, 2, 3, 4, 5, 6, 7, 8, 9 or 10.

Each of c, f, k, and p is independently 0, 1, 2, 3, 4, 5, 6, 7, 8, 9 or 10.

Each of b, j, e, h, o, and s is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100.

Each NHR moiety may optionally comprise a protecting group. In some such aspects, NHR is a polypeptide chain that includes one or more natural or unnatural α-amino acids linked together by peptide bonds having a protecting group. In such aspects, the protecting group may suitably be, without limitation, benzyl ("Bn"), t-butyl, methyl, or p-methoxybenzyl.

In some aspects, each NHR is a protected single amino acid. In some such aspects, the amino acid is aspartic acid, asparigine, arginine, histidine, lysine, glutamic acid, glutamine, serine, or homoserine. In some such aspects, the amino acid is aspartic acid or serine. In some embodiments the amino acid is D-serine having a Bn protecting group.

In some aspects, compound 5 is dibenzyl 2,2'-((3,6-diaminopyrazine-2,5-dicarbonyl)bis(azanediyl))(2R,2'R)-bis(3-hydroxypropanoate) of the following structure:

5

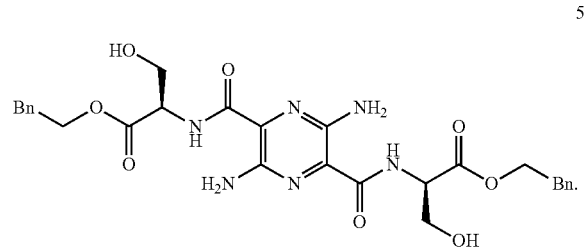 [SMILES: Nc1nc(C(=O)N[C@H](CO)C(=O)OCCc2ccccc2)c(N)nc1C(=O)N[C@H](CO)C(=O)OCCc1ccccc1]

In protecting group aspects of the present disclosure, the protecting group may be cleaved from compound 5 to form compound 6 as depicted as step 4 in FIG. 1 as follows:

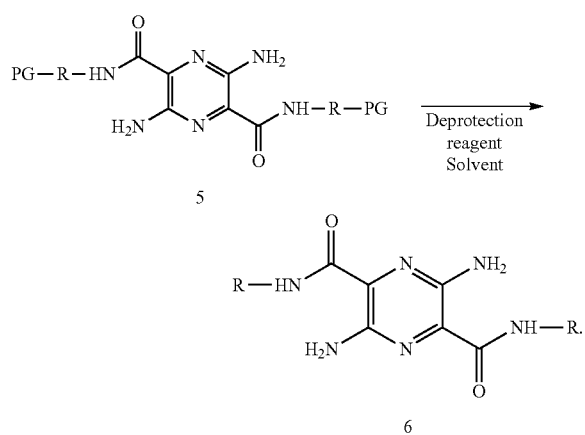

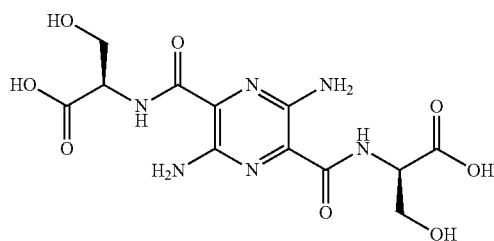

In some aspects, compound 6 is compound 6a, (2R,2'R)-2,2'-((3,6-diaminopyrazine-2,5-dicarbonyl)bis(azanediyl))bis(3-hydroxypropanoic acid), of the following structure:

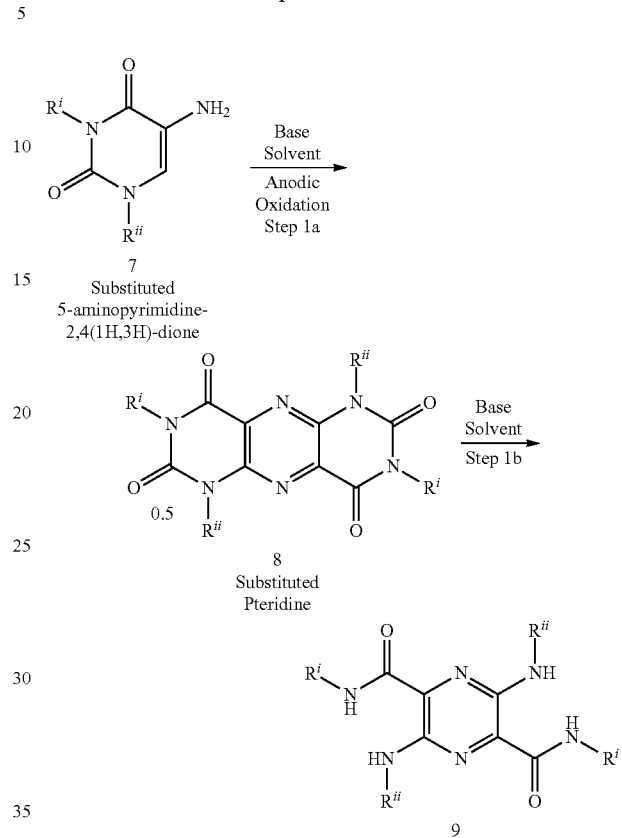

In some aspects, the solvent is a nonpolar solvent. In some aspects, the solvent is a polar solvent. In some aspects, the solvent is a polar protic solvent. Non-limiting examples of suitable polar protic solvents include water, methanol, ethanol, n-propanol, i-propanol, n-butanol, acetic acid, and combinations thereof. In some aspects, the solvent is ethanol and water.

The deprotection reagent may be a catalyst, an acid, a base, or an oxidant. Selection of a suitable deprotection reagent depends on the identity of the protecting group and the protected compound. For instance, some compounds or moieties, such as amino acids, peptides and polypeptides may be unstable in strong acid and strong base. In such aspects, a deprotection catalyst would be suitable for the practice of the present disclosure. In such aspects, a suitable catalyst could comprise a catalytically active metal such as palladium, platinum, cobalt, rhodium, nickel, ruthenium, osmium, iridium, and combinations thereof. In some aspects palladium on carbon (Pd—C) is a suitable deprotection catalyst. In some further aspects, deprotection may be done over the catalyst in the presence of hydrogen.

In some aspects, Compound 5 and Compound 6 may have a molecular weight of no more than 20000. In some such aspects, the molecular weight is no more than 15000, 14000, 13000, 12000, 11000, 10000, 9000, 8000, 7000, 6000, 5000, 4500, 4000, 3500, 3000, 2500, 2000, 1500, 1000, 900, 800, 700, 600, 500, 400 or 300. In other aspects, Compound 5 and Compound 6 may have molecular weight that is greater than 20000. In some aspects, the molecular weight is suitably from about 300 to about 1000, or from about 300 to about 750. In some aspects, Compound 6 has a molecular weight of from about 300 to about 600, or from about 300 to about 500.

The disclosure provides for an anodic process for preparing substituted pteridine compound 8, or a salt thereof, and substituted pyrazine compound 9, or a salt thereof. The reaction scheme to compound 8 is as follows:

Without being bound to any particular theory, it is believed that the anodic oxidation of the substituted 5-aminouracil compound 7 to substituted pteridine compound 8 proceeds according to the mechanism as previously disclosed, and where the pyrimidine heteroatoms that are substituted with $R^i$ and $R^{ii}$ are not atoms in the bridging ring of the formed tricyclic pteridine. Under any theory for forming substituted pteridine compound 8, it is believed that the substitution of the indicated nitrogen heteroatoms is suitable for the practice of the present disclosure because those nitrogen heteroatoms do not participate in the formation of the bridging ring in the anodic oxidation reaction. Compound 8 corresponds to the compound depicted in the mechanism prior to the keto-enol tautomerization, but where one >NH moiety is substituted with $R^i$ thereby forming $>NR^i$ and the other >NH moiety is substituted with thereby forming $>NR^{ii}$, and where ">" refers to the bonds of the hetero-nitrogen atom.

Preparation of substituted 5-amino uracil compounds, such as compound 7, is known to those skilled in the art. See, for instance, Baraldi, P. G., et al., Design, "Synthesis, and Biological Activity of Hybrid Compounds between Uramustine and DNA Minor Groove Binder Distamycin A", J. Med. Chem. 2002, 45, 3630-3638, the contents of which are incorporated herein in their entirety. For instance, in a heterocyclic substitution reaction, 5-nitropyrimidine-2,4(1H,3H)-dione may be reacted with $R^i$-leaving group and/or $R^{ii}$-leaving group in a solvent in the presence of a reducing agent to form 5-nitropyrimidine-2,4(1H,3H)-dione substituted with $R^i$ and/or $R^{ii}$ at the nitrogen heteroatoms. In some aspects, the leaving group is a halogen anion, for instance Br⁻. The substitution reaction is depicted below.

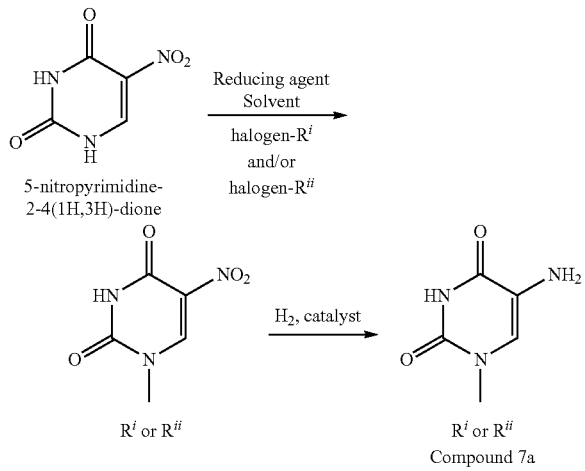

Figure 4:
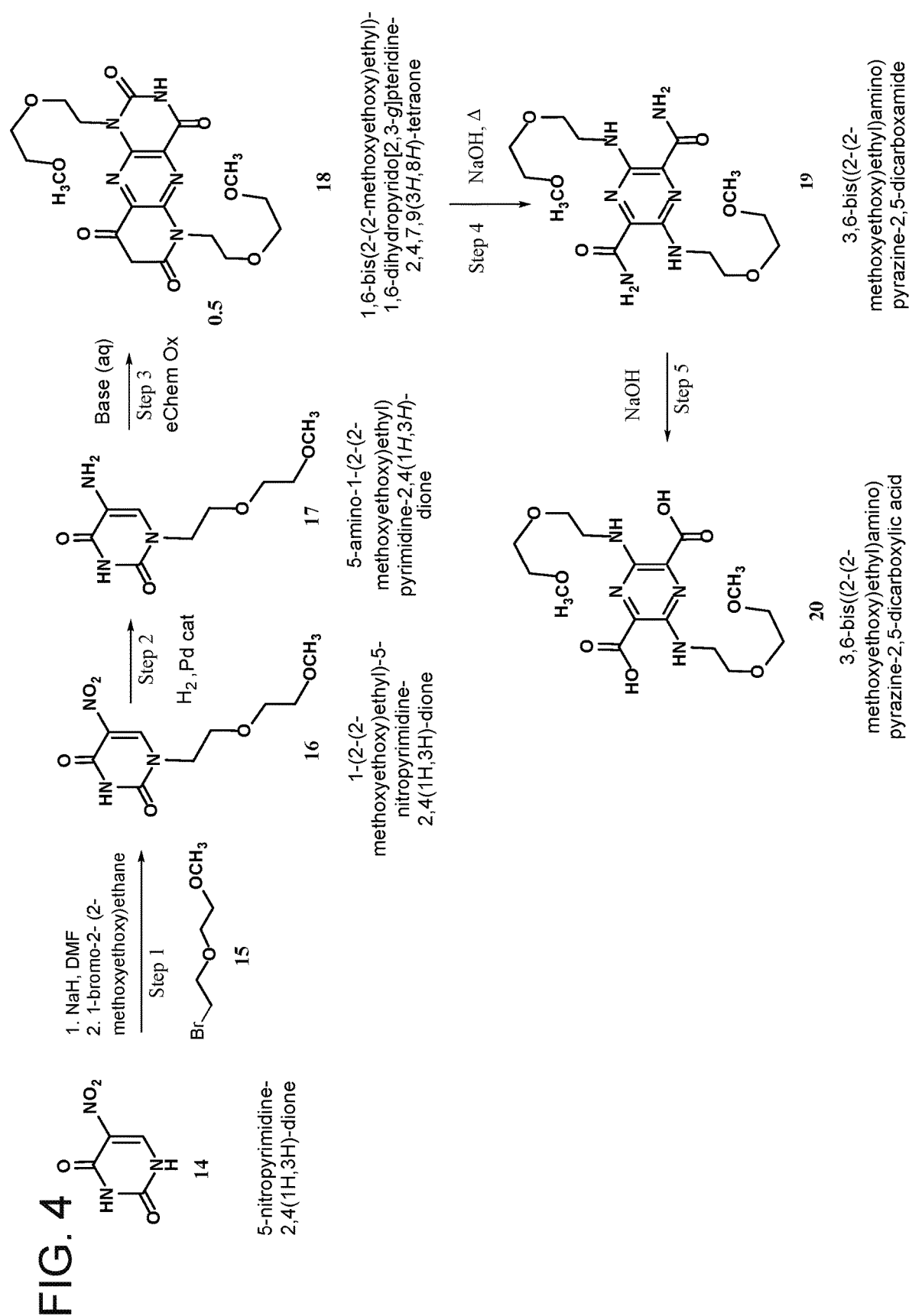
FIG. 4 depicts a proposed process for preparing a substituted pyrazine-2,5-dicarboxylic acid.

The solvent may suitably be a polar aprotic solvent such as 2-methyltetrahydrofuran, tetrahydrofuran (THF), ethyl acetate, propyl acetate (e.g., isopropyl acetate, iPrOAc), acetone, dimethylsulfoxide, N,N-dimethylformamide (DMF), acetonitrile ($CH_3CN$), N,N-dimethylacetamide, N-methylpyrrolidone (NMP), hexamethylphosphoramide, and propylene carbonate. In some aspects, the solvent is DMF. Suitable reducing agents are known in the art. In some aspects, the reducing agent is NaH. The substituted 5-nitropyrimidine-2,4(1H,3H)-dione may be reduced with hydrogen in the presence of a suitable catalyst, such as a Pd catalyst to form compound 7a. Compound 7a may then be converted to a substituted pteridine, such as compound 8, as described elsewhere herein. In one particular aspect as depicted in FIG. 4, 3,6-bis((2-(2-methoxyethoxy)ethyl)amino)pyrazine-2,5-dicarboxylic acid may be prepared from 5-nitropyrimidine-2,4(1H,3H)-dione and 1-bromo-2-(2-methoxyethoxy)ethane.

In some such aspects, compound 9 may be contacted with a base to form compound 10, or a salt thereof, as follows:

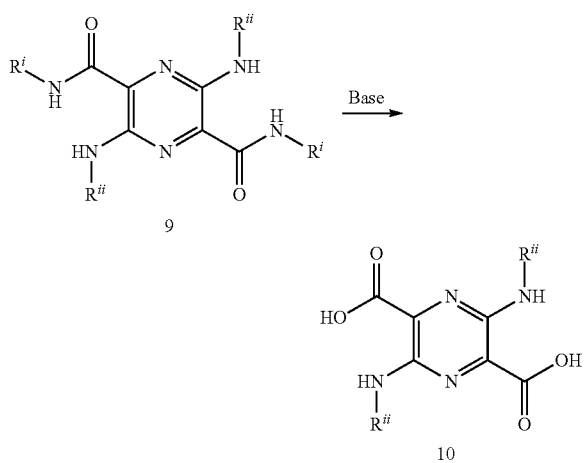

The conditions for the anodic oxidation reaction, the base and solvent are as described elsewhere herein.

$R^i$ and $R^{ii}$ are independently selected from: hydrogen, where only one of $R^i$ and $R^{ii}$ may be hydrogen; optionally substituted alkyl; optionally substituted cycloalkyl or optionally substituted heterocycloalkyl; optionally substituted aryl optionally substituted heteroaryl; optionally substituted alkoxy; optionally substituted —C(O)-alkyl; optionally substituted ester; optionally substituted amino; optionally substituted polyol ethers and optionally substituted polyethers; a polypeptide chain (AA) as described elsewhere herein; and polysaccharide chain (PS) as described elsewhere herein. In some embodiments, $R^i$ is H. In some embodiments, $R^i$ is H and $R^{ii}$ is an optionally substituted ester, such as ethyl acetate. In some embodiments, $R^i$ is H and $R_{ii}$ is an optionally substituted polyether, such as 2-(2-methoxyethoxy)ethane or a polyethylene glycol ("PEG"), such as 12 PEG.

As used herein, "alkyl" refers to a monovalent linear or branched saturated hydrocarbon moiety, consisting solely of carbon and hydrogen atoms, having from one to twenty, one to ten, one to six, or one to four carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like. Alkyl groups may be optionally substituted as defined herein.

As used herein, "cycloalkyl" refers to a carbocyclic moiety consisting of monocyclic or polycyclic rings. Cycloalkyl can optionally be substituted as defined herein. Examples of cycloalkyl moieties include, but are not limited to, cyclopropyl, cyclobutyl, cyclopentyl, cyclohexyl, cycloheptyl, and the like. Polycyclic ring structures include fused and bridged bicyclic, fused and bridged polycyclic and spirocyclic hydrocarbon ring system such as, for example, bicyclo[2.2.1]heptane, pinane, bicyclo[2.2.2]octane, adamantane, and norborene. Cycloalkyls may be saturated or partially unsaturated (e.g., cycloalkenyl).

As used herein, the term "heterocycloalkyl" refers to a saturated or partially unsaturated ring system radical having from the indicated number of overall number of stated ring atoms and containing from one to five heteroatoms selected from N, O, and S, wherein the nitrogen and sulfur atoms are optionally oxidized, nitrogen atom(s) are optionally quaternized, as ring atoms (e.g., a 3 to 12 membered heterocycloalkyl that would have 3 to 12 ring atoms and include at least one heteroatom, which also could be referred to as a $C_{2-11}$ heterocycloalkyl). Heterocycloalkyl can optionally be substituted as defined herein. A "heterocycloalkyl" ring system can be a monocyclic or a fused, bridged, or spirocyclic polycyclic (including a fused bicyclic, bridged bicyclic or spirocyclic) ring system.

As used herein, "aryl" refers to a monovalent aromatic hydrocarbon radical of 6-20 carbon atoms ($C_6$-$C_{20}$). Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein. In some aspects, aryl may be substituted with alkyl, cycloalkyl, halogen, or haloalkyl. Alkyl may be substituted directly to a heteronitrogen or may be linked to the heteronitrogen by an alkyl or substituted alkyl.

As used herein, the term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Heteroaryl groups are optionally substituted independently with one or more substituents described herein.

As used herein, "alkoxy" refers to a moiety of the structure —OR, wherein R is an alkyl moiety as defined herein. Examples of alkoxy moieties include, but are not limited to, methoxy, ethoxy, isopropoxy, and the like.

As used herein, "haloalkyl" refers to an alkyl as defined herein in which one or more hydrogen atoms have been replaced with the same or a different halogen. Exemplary haloalkyls include —$CH_2Cl$, —$CH_2CF_3$, —$CH_2CCl_3$, —$CF_3$, $CHF_2$, and the like.

As used herein, "—C(O)-alkyl" refers to an optionally substituted aldehyde moiety that forms an amide with the heteronitrogen, i.e., >N—C(O)-alkyl. Non-limiting examples of substituted N—C(O)-alkyl includes amide-ol, amide-diol, amide-polyol, and derivatives thereof.

As used herein, "polyol ethers" and "poly ethers" are of the general structure where the hetero-nitrogen refers to the ring atom to which the polyol ether or poly ether is bound

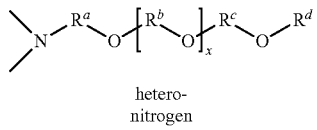

hetero-
nitrogen where: $R^a$ is optionally substituted $C_{1-4}$ alkyl; $R^b$ is optionally substituted $C_{1-4}$ alkyl; $R^c$ is optionally substituted $C_{1-4}$ alkyl; and $R^d$ is optionally substituted $C_{1-4}$ alkyl or hydrogen. x is 1, 2, 3, 4, 5, 10, 15, 20, 25, 30, 35, 40, 45, 50, 60, 70, 80, 90, or 100, and any range constructed therefrom, such as for instance from 1 to 100, from 1 to 70, from 1 to 50, from 1 to 30, from 1 to 20, from 2 to 20, from 2 to 10, from 3 to 20, from 3 to 10, from 5 to 20, or from 5 to 10. In some aspects, $R^a$ to $R^c$ are each $C_2$ and $R^d$ is H or $C_{1-2}$. In one example, the polyether is PEG. In some non-limiting aspects, branched polyols and branched polyethers are of the general structure below where the hetero-nitrogen refers to the ring atom to which the polyol ether or poly ether is bound

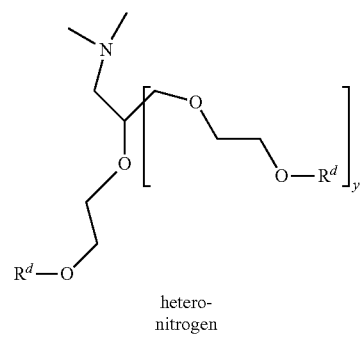

hetero-
nitrogen where $R^d$ is as defined herein, and y is 1, 2, 3, 4, 5, 10, 15, 20, 25, 30, 35, 40, 45, or 50, and any range constructed therefrom, such as for instance from 1 to 50, from 1 to 30, from 1 to 20, from 2 to 20, from 2 to 10, from 3 to 20, from 3 to 10, from 5 to 20, or from 5 to 10. Non-limiting examples include the following structures where the hetero-nitrogen refers to the ring atom to which the polyol ether or poly ether is bound

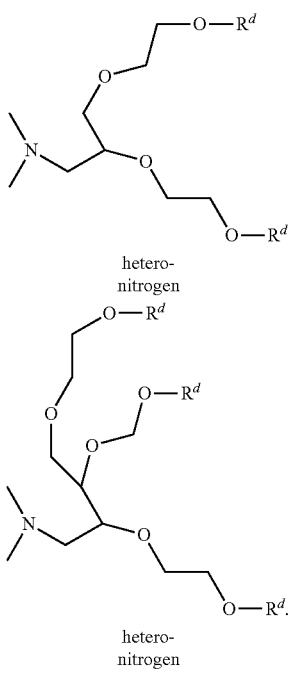

hetero-
nitrogen

As used herein, "halogen" refers to chlorine, fluorine, bromine and iodine.

As used herein, "amino" refers to a moiety of the structure —$NR^xR^y$ wherein $R^x$ and $R^y$ are each hydrogen, "monoalkylamino" refers to such a structure where one of $R^x$ and $R^y$ is hydrogen and the other of $R^x$ and $R^y$ is alkyl, and "dialkylamino" refers to such a structure where each of $R^x$ and $R^y$ is alkyl.

As used herein, "optionally substituted" as used herein refers to a moiety that may be unsubstituted or substituted with specific groups. Examples of substituents include, but are not limited to hydroxy, alkyl, alkoxy, halo, haloalkyl, oxo, amino, monoalkylamino, or dialkylamino.

In some such aspects, compound 10, or a salt thereof, may be reacted with NHR acid salt (compound 4) in a solvent to form compound 11, or a salt thereof, as follows:

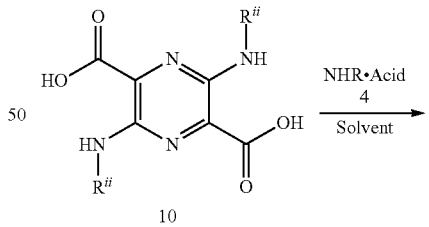

10

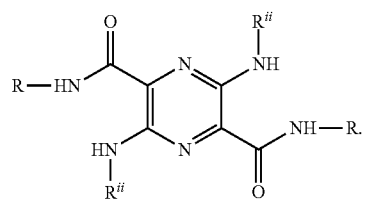

11

R and $R^{ii}$ and the reaction are previously defined in connection with the preparation of compound 5 by the reaction of compound 3 with compound 4.

In aspects of the disclosure each HNR moiety comprises a protecting group, PG, and said protecting group is cleaved to form compound 13 as follows and as described elsewhere herein in connection with compounds 5 and 6.

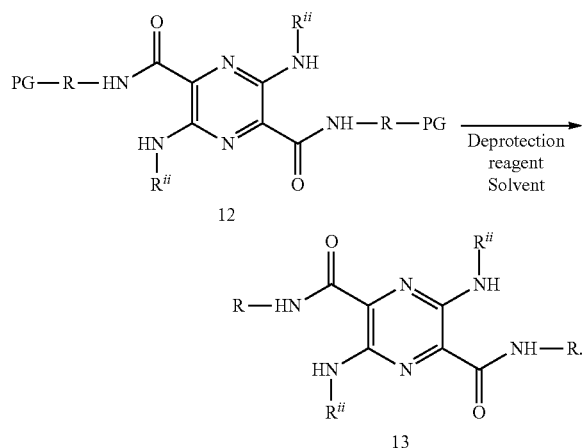

12

13

EXAMPLES

Example 1

Potassium 4,9-dihydroxypyrimido[4,5-g]pteridine-2,7-bis(olate) was prepared according to the following reaction scheme:

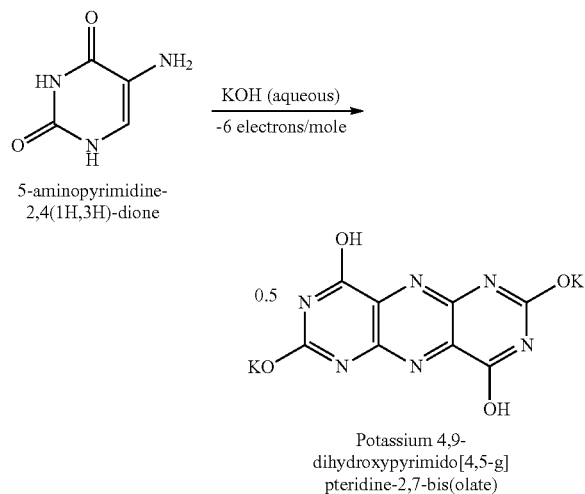

5-aminopyrimidine-2,4(1H,3H)-dione

Potassium 4,9-dihydroxypyrimido[4,5-g]pteridine-2,7-bis(olate)

In a first (anode) chamber, the inside wall of a Berzelius beaker (tall form, 400 mL) was fitted a platinum coated titanium expanded mesh screen and a graphite felt anode was placed uniformly over it and lining the inner wall. A stainless steel cathode formed from 0.25 inch tubing was placed in a separate (cathode) chamber formed from a pvc tube having an outer diameter of about ¾ inch (1.9 cm) and a length of about 6 inches (15.24 cm) that was sealed at one end with clear silicone room temperature vulcanizing ("RTV"). The tube was perforated by drilling evenly spaced ¼ inch (0.64 cm) holes to a distance of about 4 inches (10.2 cm) from the bottom of an RTV plug. Nafion N324 membrane, 0.15 mm (0.006 inches) thick, Teflon™ fabric reinforced (Rf[OCF$_2$CF(CF$_3$)$_2$]$_n$OCF$_2$CF$_2$SO$_3$H) was wrapped around the pvc supporting tube with the coarse side facing the cathode, and then sealed with silicone RTV while being careful not to contaminate the exposed Nafion surface with RTV. The Nafion membrane was configured to enclose the tube and prevent mixing between the two chambers, but allowing for charge transfer between the two chambers. The Nafion membrane was pre-treated by immersion (agitated by swirling the solution by hand) in a KOH solution contained in a 100 mL graduated cylinder. The membrane initially shrunk to about one half its original diameter, but then expanded until it contacted the wall of the graduated cylinder. The membrane was allowed to soak for greater than 0.5 hour. It was thereafter removed and rinsed with deionized water. The membrane was kept moist by storing in a plastic baggie. The cell was constructed so that the graphite felt anode had about a 0.5 inch (1.27 cm) space at the bottom into which was placed a magnetic stir bar. The cathode chamber tube was suspended in the middle of the beaker (anode) assembly by attaching it to a three-pronged clamp.

The assembled 2-chamber cell was filled with an aqueous solution of KOH (4.2 g KOH in 160 mL deionized water) so that both chambers were filled to an approximately equal level. 5-aminopyrimidine-2,4(1H,3H)-dione (5-aminouracil) (2.0 g, 0.0157 mole) was added to the anolyte and allowed to dissolve. A DC power supply (Lambda, Model LG-532) was connected, and 1.0 A (5.6 V) was passed through the cell with continuous stirring until two Faradays of charge had passed (0.9 hrs). The anolyte turned red during the course of the reaction (from its initial yellow color).

The anolyte and catholyte were each analyzed for the presence of the desired product by reverse phase high performance liquid chromatography ("reHPLC"). The anolyte was confirmed to exhibit a significant amount of potassium 4,9-dihydroxypyrimido[4,5-g]pteridine-2,7-bis(olate). The catholyte was found to not contain a detectable amount of potassium 4,9-dihydroxypyrimido[4,5-g]pteridine-2,7-bis(olate).

Example 2

3,6-diaminopyrazine-2,5-dicarboxylic acid was prepared from potassium 4,9-dihydroxypyrimido[4,5-g]pteridine-2,7-bis(olate) according to the following reaction scheme:

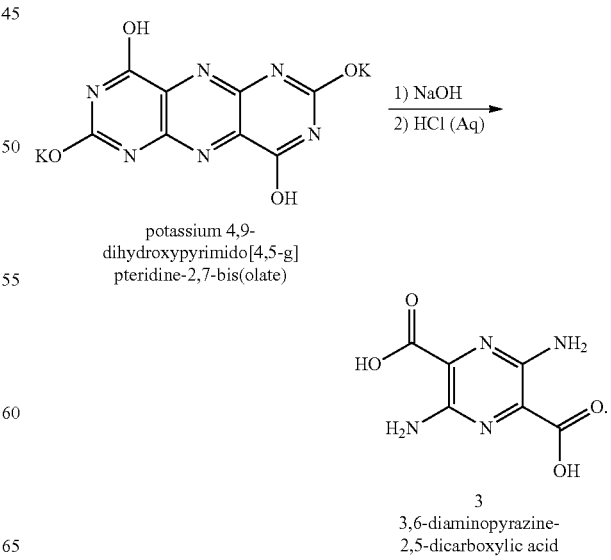

potassium 4,9-dihydroxypyrimido[4,5-g]pteridine-2,7-bis(olate)

3

3,6-diaminopyrazine-2,5-dicarboxylic acid

In each of two Teflon reaction vessels was placed 0.5 g of potassium 4,9-dihydroxypyrimido[4,5-g]pteridine-2,7-bis (olate), and a solution containing 0.3 to 0.4 g sodium hydroxide in 10 mL deionized water. The vessels were secured in a microwave reactor and allowed to react for one hour at 170° C. and at about 100 psig pressure. The vessels were allowed to cool to about 50° C., and the contents were filtered to remove a small amount of solid residue. The bright yellow filtrate was transferred to a 250 mL round-bottomed flask equipped with a large magnetic stir bar. The pH was adjusted with stirring to about 3 with concentrated HCl forming a large amount of red precipitate. A few more drops of acid were added and the solid was collected by filtration on a glass frit, wash with cold 1N HCl (1×10 mL), acetonitrile (2×30 mL) and diethyl ether (1×30 mL), suctioned dry, and transferred to vacuum oven. The collected solid was dried overnight at 45-50° C. to yield 0.48 g 3,6-diaminopyrazine-2,5-dicarboxylic acid (79%). $C^{13}$ NMR ($D_2O$/NaOD, external TMS reference) δ 132.35, 147.32, 171.68.

Example 3

An IKA ElectraSyn Pro-Divide two compartment cell equipped with a 5 u porous polypropylene frit divider and stir bars was charged with 5-aminouracil potassium salt (0.10 g) in 13.0 mL deionized water, with 6.5 mL in each of the two cell compartments. The anode was reticulated foam carbon and the anode compartment was fitted with a thermocouple. The cathode was stainless steel.

The oxidation was carried out under constant current conditions (13 mA) for 100 minutes at which point 62% of the 5-aminouracil had been consumed. The major product, 1,6-dihydropyrimido[4,5-g]pteridine-2,4,7,9(3H,8H)-tetraone was quantified by HPLC and determined to have been produced in 22% yield (7 mg) based on consumed 5-aminouracil).

Example 4

The conditions of Example 3 were repeated except the anode was replaced with a reticulated foam carbon anode of the same dimensions. The reaction progress was checked at 32% conversion of 5-aminouracil and was determined to have produced 11.2 mg of 1,6-dihydropyrimido[4,5-g]pteridine-2,4,7,9(3H,8H)-tetraone.

Example 5

The conditions of Example 4 were repeated, but the polarity of the electrodes was reversed every 10 seconds. The yield of 1,6-dihydropyrimido[4,5-g]pteridine-2,4,7,9 (3H,8H)-tetraone was 26% based on the amount of 5-aminouracil consumed.

Example 6

The conditions of Example 3 were repeated, but 27 mg of potassium ferrocyanide was added to the anolyte. The yield of 1,6-dihydropyrimido[4,5-g]pteridine-2,4,7,9(3H,8H)-tetraone was 39.2% based on the amount of 5-aminouracil consumed.

Example 7

The conditions of Example 3 were repeated, but controlled anode potential conditions were employed instead of the controlled current conditions used in Example 3. The anode potential was held to 1.2 V vs. Ag°/AgCl reference. After 140 minutes, a 41% yield of 1,6-dihydropyrimido[4,5-g]pteridine-2,4,7,9(3H,8H)-tetraone was obtained by quantitative rpHPLC analysis based on the amount of 5-aminouracil consumed.

Example 8

The conditions of Example 3 were repeated, except the anode was replaced with the following materials, each in an independent experiment: glassy carbon, graphite, and platinum. A yield of 1,6-dihydropyrimido[4,5-g]pteridine-2,4,7,9(3H,8H)-tetraone similar to Example 3 was obtained for each of the evaluated anodes.

Example 9

The conditions of Example 3 were repeated, except the porous polypropylene frit divider was removed thereby providing an undivided cell. A yield of 1,6-dihydropyrimido [4,5-g]pteridine-2,4,7,9(3H,8H)-tetraone of 10% was achieved based on the amount of consumed 5-aminouracil.

Example 10 (Prophetic): Preparation of 1,6-bis(2-(2-methoxyethoxy)ethyl)-1,6-dihydropyrimido[4,5-g]pteridine-2,4,7,9(3H,8H)-tetraone (14)

As depicted in FIG. 4, in step 1, 5-nitropyrimidine-2,4 (1H,3H)-dione (14) may be reacted with 1-bromo-2-(2-methoxyethoxy)ethane (15) according to the procedure of Baraldi, P. G., et al., J. Med. Chem., 2002, 45, 3630-3638 that is outlined in the Experimental Section under the General Procedure for the Synthesis of Compounds 4-9 found on page 3634, thereby producing 1-(2-(2-methoxyethoxy)ethyl)-5-nitropyrimidine-2,4(1H,3H)-dione (16).

As depicted in FIG. 4, in step 2, compound 16 may be reduced to 5-amino-1-(2-(2-methoxyethoxy)ethyl) pyrimidine-2,4(1H,3H)-dione (17) using 10% Pd on carbon and hydrogen in a suitable solvent, such as 2-methoxyethanol, using substantially the conditions of Baraldi, General Procedure for the Synthesis of Compounds 10-15 in the reference cited in Step 1, page 3635.

As depicted in FIG. 4, in step 3, Electrochemical anodic oxidation of 5-amino-1-(2-(2-methoxyethoxy)ethyl) pyrimidine-2,4(1H,3H)-dione (17) may be done using substantially the conditions of Examples 1-9 would produce 1,6-bis(2-(2-methoxyethoxy)ethyl)-1,6-dihydropyrimido[4,5-g]pteridine-2,4,7,9(3H,8H)-tetraone (18) that may be isolated by reverse phase high pressure liquid chromatography, by rpHPLC, or by precipitation techniques known in the art.

Example 11 (Prophetic): Preparation of 3,6-bis((2-(2-methoxyethoxy)ethyl)amino)pyrazine-2,5-dicarboxylic acid (20)

As further depicted in FIG. 4, 1,6-bis(2-(2-methoxyethoxy)ethyl)-1,6-dihydropyrimido[4,5-g]pteridine-2,4,7,9 (3H,8H)-tetraone (18) may be converted to 3,6-bis((2-(2-methoxyethoxy)ethyl)amino)pyrazine-2,5-dicarboxylic acid (20) may be effected using substantially the conditions of Example 2.

Example 12 (Prophetic): Preparation of Preparation of diethyl 2,2'-(2,4,7,9-tetraoxo-2,3,4,7,8,9-hexahydropyrimido[4,5-g]pteridine-1,6-diyl)diacetate (24)

Figure 5:
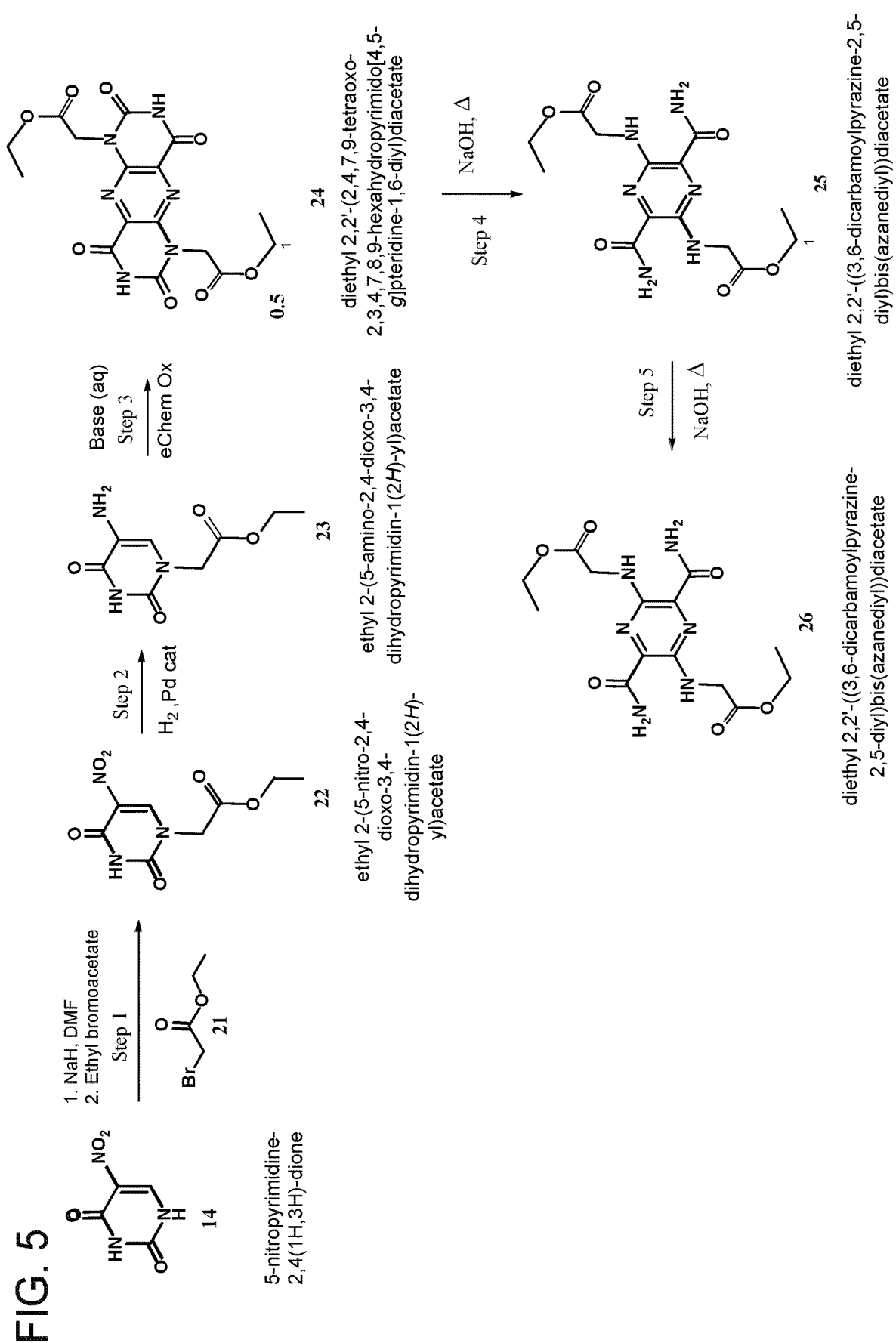
FIG. 5 depicts a proposed process for preparing a substituted pyrazine-2,5-dicarboxylic acid.

As depicted in FIG. 5, in step 1, 5-nitropyrimidine-2,4 (1H,3H)-dione (14) may be reacted with ethyl bromoacetate

(21) according to the procedure of Baraldi, that is outlined in the Experimental Section under the General Procedure for the Synthesis of Compounds 4-9 found on page 3634, thereby producing ethyl 2-(5-nitro-2,4-dioxo-3,4-dihydropyrimidin-1(2H)-yl)acetate (22).

As depicted in FIG. 5, in step 2, Compound 22 may be reduced to ethyl 2-(5-amino-2,4-dioxo-3,4-dihydropyrimidin-1(2H)-yl)acetate (23) using 10% Pd on carbon and hydrogen in a suitable solvent, such as 2-methoxyethanol, using substantially the conditions of General Procedure for the Synthesis of Compounds 10-15 in the reference cited in Step 1, page 3635.

As depicted in FIG. 5, in step 3, electrochemical anodic oxidation of ethyl 2-(5-amino-2,4-dioxo-3,4-dihydropyrimidin-1(2H)-yl)acetate (23) may be done using substantially the conditions of Examples 1-9 would produce diethyl 2,2'-(2,4,7,9-tetraoxo-2,3,4,7,8,9-hexahydropyrimido[4,5-g]pteridine-1,6-diyl)diacetate (24) that may be isolated by rpHPLC, normal phase silica gel chromatography or by precipitation techniques known in the art.

Example 13 (Prophetic): Production of diethyl 2,2'-((3,6-dicarbamoylpyrazine-2,5-diyl)bis(azanediyl)) diacetate (26)

As further indicated in FIG. 5, conversion of diethyl 2,2'-(2,4,7,9-tetraoxo-2,3,4,7,8,9-hexahydropyrimido[4,5-g]pteridine-1,6-diyl)diacetate (24) to diethyl 2,2'4(3,6-dicarbamoylpyrazine-2,5-diyl)bis(azanediyl))diacetate (26) may be effected using substantially the conditions of Example 2.

Example 14 (Prophetic): Production of Preparation of 1,6-di(2,5,8,11,14,17,20,23,26,29,32,35-dodecaoxaheptatriacontan-37-yl)-1,6-dihydropyrimido[4,5-g]pteridine-2,4,7,9(3H,8H)-tetraone (32)

As depicted in FIG. 6, step 1, 5-nitropyrimidine-2,4(1H,3H)-dione (14) may be reacted with m-12 PEG-bromide (27) according to the procedure of Baraldi, that is outlined in the Experimental Section under the General Procedure for the Synthesis of Compounds 4-9 found on page 3634, thereby producing 1-(2,5,8,11,14,17,20,23,26,29,32,35-dodecaoxaheptatriacontan-37-yl)-5-nitropyrimidine-2,4(1H,3H)-dione (28).

As depicted in FIG. 6, step 2, compound 24 may be reduced to 5-amino-1-(2,5,8,11,14,17,20,23,26,29,32,35-dodecaoxaheptatriacontan-37-yl)pyrimidine-2,4(1H,3H)-dione (29) using 10% Pd on carbon and hydrogen in a suitable solvent, such as 2-methoxyethanol, and substantially the conditions of Baraldi for the Synthesis of Compounds 10-15 in the reference cited in Step 1, page 3635.

As depicted in FIG. 6, step 3, electrochemical anodic oxidation of 5-amino-1-(2,5,8,11,14,17,20,23,26,29,32,35-dodecaoxaheptatriacontan-37-yl)pyrimidine-2,4(1H,3H)-dione (29) using substantially the conditions of Examples 1-9 would produce 1,6-di(2,5,8,11,14,17,20,23,26,29,32,35-dodecaoxaheptatriacontan-37-yl)-1,6-dihydropyrimido[4,5-g]pteridine-2,4,7,9(3H,8H)-tetraone (30) that may be isolated by rpHPLC, normal phase silica gel chromatography or by precipitation techniques known in the art.

Example 15 (Prophetic): Preparation of 1,6-di(2,5,8,11,14,17,20,23,26,29,32,35-dodecaoxaheptatriacontan-37-yl)-1,6-dihydropyrimido[4,5-g]pteridine-2,4,7,9(3H,8H)-tetraone (32)

As further depicted in FIG. 6, conversion of 1,6-di(2,5,8,11,14,17,20,23,26,29,32,35-dodecaoxaheptatriacontan-37-yl)-1,6-dihydropyrimido[4,5-g]pteridine-2,4,7,9(3H,8H)-tetraone (30) to 1,6-di(2,5,8,11,14,17,20,23,26,29,32,35-dodecaoxaheptatriacontan-37-yl)-1,6-dihydropyrimido[4,5-g]pteridine-2,4,7,9(3H,8H)-tetraone (32) may be effected using substantially the conditions of Example 2.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A process for preparing divalent salts of pyrimido[4,5-g]pteridine-2,4,7,9-tetraol, Compound 2, the process comprising step 1a directed to anodic oxidation of 5-aminopyrimidine-2,4(1H,3H)-dione, Compound 1, in the presence of an aqueous base to form pyrimido[4,5-g]pteridine-2,4,7,9-tetraol, Compound 2a, followed by step 1b directed to treatment of compound 2a with a base to form Compound 2 as follows:

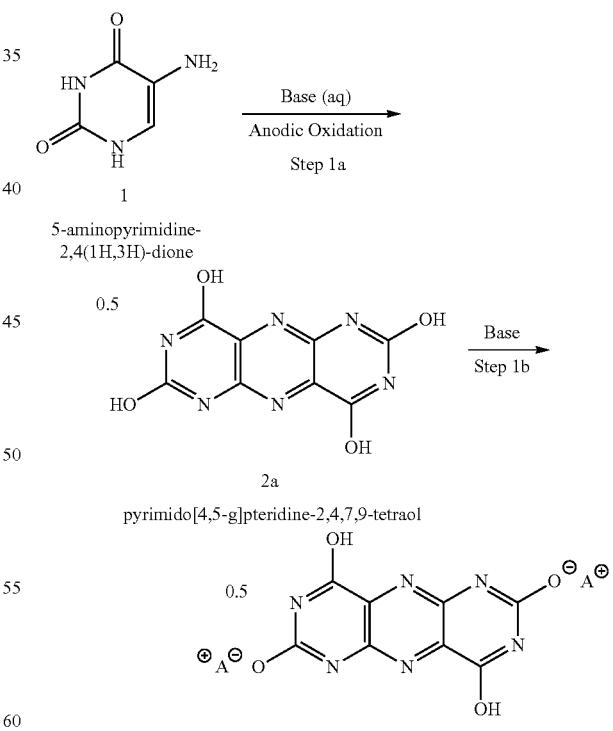

wherein A$^+$ is a monovalent cation.

2. The process of claim 1, wherein the base in step 1b is KOH and compound 2 is potassium 4,9-dihydroxypyrimido[4,5-g]pteridine-2,7-bis(olate) of the structure:

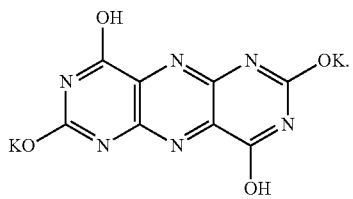

2

3. The process of claim 1, wherein steps 1a and 1b are done in an electrochemical cell.

4. The process of claim 3, wherein the electrochemical cell comprises divided cells.

5. The process of claim 3, wherein the electrochemical cell comprises undivided cells.

6. The process of claim 1, further comprising hydrolyzing Compound 2, in the presence of a base to form 3,6-diaminopyrazine-2,5-dicarboxylic acid, Compound 3, as follows:

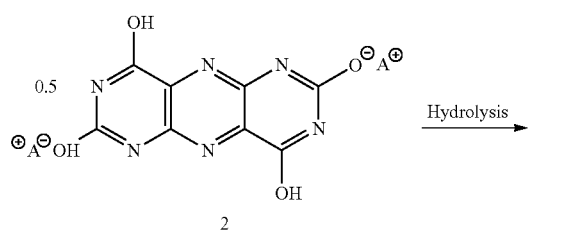

2

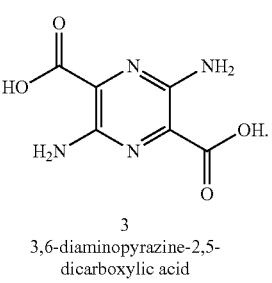

3
3,6-diaminopyrazine-2,5-
dicarboxylic acid

7. The process of claim 6, further comprising reacting 3,6-diaminopyrazine-2,5-dicarboxylic acid with an acid salt of NHR, Compound 4, to form Compound 5, as follows:

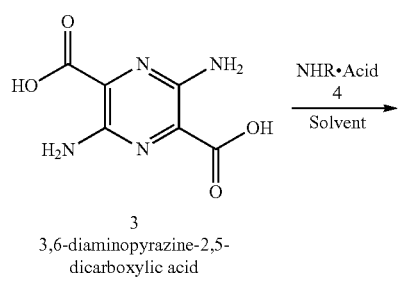

3
3,6-diaminopyrazine-2,5-
dicarboxylic acid $\xrightarrow{\text{NHR·Acid}\atop\text{Solvent}}$ -continued

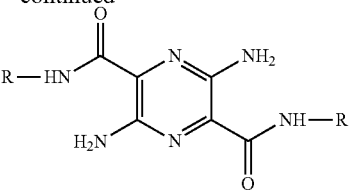

5 wherein each NHR is independently
(i) a polypeptide chain that includes one or more natural or unnatural α-amino acids linked together by peptide bonds, or
(ii) $NH(R^1)(R^2)$ wherein:
each $R^1$ is independently $-(CH_2)_a(CH_2CH_2O)_b(CH_2)_c NR^{10}CONR^{11}(CH_2)_d(CH_2CH_2O)_eR^{20}$, $-(CH_2)_a(CH_2CH_2O)_b(CH2)_cNR^{12}CSNR^{13}(CH_2)_d (CH_2CH_2O)_eR^{21}$, $-(CH_2)_a(CH_2CH_2O)_b(CH_2)_c CONR^{14}(CH_2)_d(CH_2CH_2O)_eR^{22}$, $-(CH_2)_a (CH_2CH_2O)_b(CH_2)_cNR^{15}SO_2(CH_2)_d(CH_2CH_2O)_e R^{23}$, $-(CH_2)_a(CH_2CH_2O)_b(CH_2)_cSO_2NR^{16}(CH_2)_a (CH_2CH_2O)_eR^{24}$, $-(CH2)_a(CH_2CH_2O)_b(CH_2)_c NR^{17}CO(CH_2)_d(CH_2CH_2O)_eR^{25}$, $-(CH2)_a (CH_2CH_2O)_b(CH_2)_cNR^{18}CO_2(CH_2)_d(CH_2CH_2O)_e R^{26}$, or $-(CH_2)_a(CH_2CH_2O)_b(CH_2)_cOC(O) NR^{19}CO_2(CH_2)_d(CH_2CH_2O)_eR^{27}$; $-(CH_2)_cOR^{68}$, $-CH_2(CHOH)_cR^{69}$, $-CH_2(CHOH)_cCO_2H$, $-(CHCO_2H)_cCO_2H$, $-(CH_2)_cNR^{70}R^{71}$, $-CH [(CH_2)_cNH_2]_cCO_2H$, $-CH[(CH_2)_cNH_2]_cCH_2OH$, $-CH_2(CHNH_2)_cCH2NR^{72}R^{73}$, $-(CH_2CH_2O)_eR^{74}$, $-(CH_2)_tCO(CH_2CH_2O)_eR^{75}$, $-(CH_2)_u (CH_2CH_2O)_j(CH_2)_kNR^{58}C(O)NR^{59}(CH_2)_l (CH_2CH_2O)_oR^{76}$, $-(CH_2)_u(CH_2CH_2O)_j(CH_2)_k NR^{60}C(S)NR^{61}(CH_2)_l(CH_2CH_2O)_oR^{77}$, $-(CH_2)_u (CH_2CH_2O)_j(CH_2)_kC(O)NR^{62}(CH_2)_l(CH_2CH_2O)_o R^{78}$, $-(CH_2)_u(CH_2CH_2O)_j(CH_2)_kS(O)_2NR^{63}(CH_2)_l (CH_2CH_2O)_oR^{79}$, $-(CH_2)_u(CH_2CH_2O)_j(CH_2)_k NR^{64}S(O)_2(CH_2)_l(CH_2CH_2O)_oR^{80}$, $-(CH_2)_u (CH_2CH_2O)_j(CH_2)_kNR^{65}C(O)(CH_2)_l(CH_2CH_2O)_o R^{81}$, $-(CH_2)_u(CH_2CH_2O)_j(CH_2)_kNR^{66}C(O)O (CH_2)_l(CH_2CH_2O)_oR^{82}$, or $-(CH_2)_u(CH_2CH_2O)_j (CH_2)_kOC(O)NR^{67}(CH_2)_l(CH_2CH_2O)_oR^{83}$, $-(CH_2)_aSO_3H$, $-(CH_2)_aSO_3^-$, $-(CH_2)_aOSO_3H$, $-(CH_2)_aOSO_3^-$, $-(CH_2)_aNHSO_3H$, $-(CH_2)_a NHSO_3^-$, $-(CH_2)_aPO_3H_2$, $-(CH_2)_aPO_3H^-$, $-(CH_2)_aPO_3^=$, $-(CH_2)_aOPO_3H_2$, $-(CH_2)_a OPO_3H^-$, or $-(CH_2)_aOPO^{3-}$;
each of $R^2$, $R^{10}$, $R^{11}$, $R^{12}$, $R^{13}$, $R^{14}$, $R^{15}$, $R^{16}$, $R^{17}$, $R^{18}$, $R^{19}$, $R^{58}$, $R^{59}$, $R^{60}$, $R^{61}$, $R^{62}$, $R^{63}$, $R^{64}$, $R^{65}$, $R^{66}$ and $R^{67}$ is independently $-H$ or $-CH_3$;
each of $R^{20}$, $R^{21}$, $R^{22}$, $R^{23}$, $R^{24}$, $R^{25}$, $R^{26}$, and $R^{27}$ is independently $-H$, $-CH_3$, $-(CH_2)_fNR^{28}C(O) NR^{29}(CH_2)_g(CH_2CH_2O)_hR^{38}$, $-(CH_2)_f NR^{30}CSNR^{31}(CH_2)_g(CH_2CH_2O)_hR^{39}$, $-(CH_2)_fC (O)NR^{32}(CH_2)_g(CH_2CH_2O)_hR^{40}$, $-(CH_2)_fS(O)_2 NR^{33}(CH_2)_g(CH_2CH_2O)_hR^{41}$, $-(CH_2)_fNR^{34}S(O)_2 (CH_2)_g(CH_2CH_2O)_hR^{42}$, $-(CH_2)_fNR^{35}C(O)(CH_2)_g (CH_2CH_2O)_hR^{43}$, $-(CH_2)_fNR^{36}C(O)O(CH_2)_g (CH_2CH_2O)_hR^{44}$, $-(CH_2)_fOC(O)NR^{37}(CH_2)_g (CH_2CH_2O)_hR^{45}$, $-CO(AA)$, or $-CONH(PS)$;
each of $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ is independently $-H$ or $-CH_3$; each of $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, and $R^{80}$ is independently $-H$, $-CH_3$, $-(CH_2)_pS$ $(O)_2NR^{84}(CH_2)_q(CH_2CH_2O)_sR^{81}$, $—(CH_2)_pNR^{85}S(O)_2(CH_2)_q(CH_2CH_2O)_sR^{83}$, $—(CH_2)_pNR^{86}C(O)(CH_2)_q(CH_2CH_2O)_sR^{85}$, $—(CH_2)_pNR^{86}C(O)O(CH_2)_q(CH_2CH_2O)_sR^{87}$, or $—(CH_2)_pOC(O)NR^{88}(CH_2)_q(CH_2CH_2O)_sR^{89}$;

each of $R^{81}$, $R^{82}$, $R^{83}$, $R^{84}$, $R^{85}$, $R^{86}$, $R^{87}$, $R^{88}$, and $R^{89}$ is independently —H or —CH$_3$;

each (AA) is independently a polypeptide chain that includes one or more natural or unnatural α-amino acids linked together by peptide bonds;

each (PS) is independently a sulfated or non-sulfated polysaccharide chain comprising one or more monosaccharide units connected by glycosidic linkages;

each of t and u is independently 1, 2, 3, 4, or 5;

each of a, d, g, 1, and q is independently 0, 1, 2, 3, 4, 5, 6, 7, 8, 9 or 10;

each of c, f, k, and p is independently 0, 1, 2, 3, 4, 5, 6, 7, 8, 9 or 10; and each of b, j, e, h, o, and s is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100, wherein each NHR moiety optionally comprises a protecting group.

8. The process of claim 7, wherein NHR is D-serine comprising a benzyl protecting group.

9. The process of claim 7, wherein each NHR moiety comprises a protecting group, PG, and wherein said protecting group is cleaved to form compound 6 as follows:

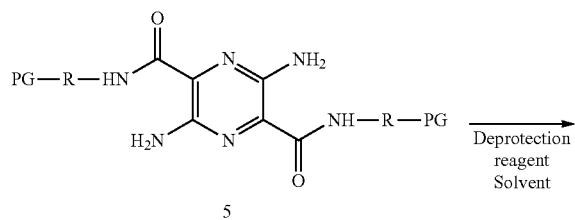

10. The process of claim 9, wherein NHR is D-serine and compound 6 is (2R,2'R)-2,2'-((3,6-diaminopyrazine-2,5-dicarbonyl)bis(azanediyl))bis(3-hydroxypropanoic acid) of the following structure:

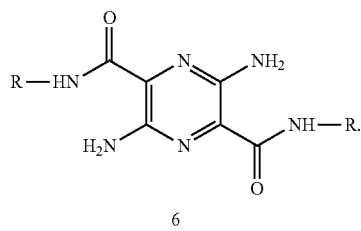

11. A process for preparing a substituted pteridine compound, the process comprising step 1a directed to anodic oxidation of compound 7, or a salt thereof, in the presence of a base and a solvent to form compound 8, or a salt thereof, as follows:

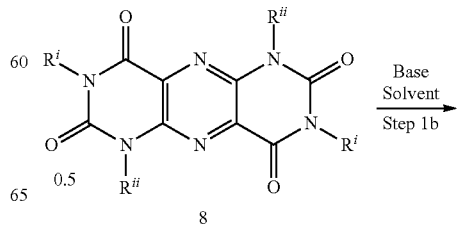

wherein $R^i$ and $R^{ii}$ are independently selected from: hydrogen, where only one of $R^i$ and $R^{ii}$ may be hydrogen; optionally substituted alkyl; optionally substituted ester; optionally substituted cycloalkyl or optionally substituted heterocycloalkyl; optionally substituted aryl or optionally substituted heteroaryl; optionally substituted alkoxy; optionally substituted —C(O)—alkyl; optionally substituted amino; optionally substituted polyol ethers and optionally substituted polyethers; a polypeptide chain (AA); and polysaccharide chain (PS).

12. The process of claim 11, further comprising step 1b directed to contacting compound 8, or a salt thereof, with a base in the presence of a solvent to form pyrazine compound 9, or a salt thereof, as follows

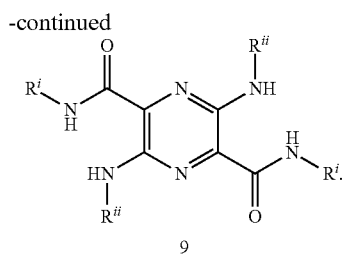

13. The process of claim 12, further comprising contacting compound 9, or a salt thereof, with a base in the presence of a solvent to form pyrazine compound 10, or a salt thereof, as follows

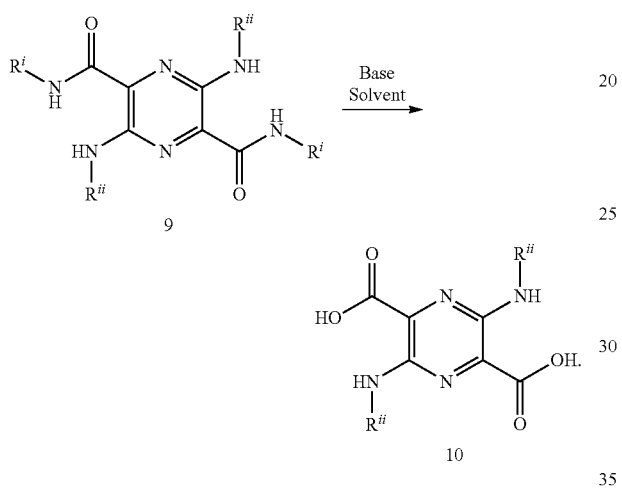

14. The process of claim 10, further comprising reacting compound 10, or a salt thereof, with NHR acid salt compound 4 in a solvent to form compound 11, or a salt thereof, as follows:

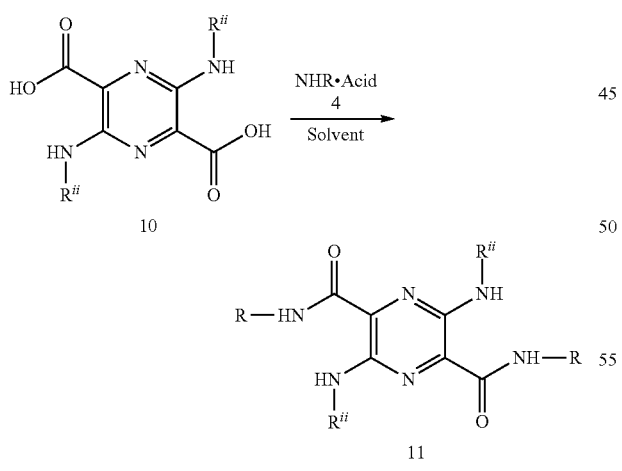

wherein each NHR is independently
(i) a polypeptide chain that includes one or more natural or unnatural α-amino acids linked together by peptide bonds, or
(ii) NH($R^1$)($R^2$) wherein:
each $R^1$ is independently —$(CH_2)_a(CH_2CH_2O)_b(CH_2)_c$ $NR^{10}CONR^{11}(CH_2)_d(CH_2CH_2O)_eR^{20}$, —$(CH_2)_a$ $(CH_2CH_2O)_b(CH2)_cNR^{12}CSNR^{13}(CH_2)_d(CH_2CH_2 O)_eR^{21}$, —$(CH_2)_a(CH_2CH_2O)_b(CH_2)_cCONR^{14}$ $(CH_2)_d(CH_2CH_2O)_eR^{22}$, —$(CH_2)_a(CH_2CH_2O)_b$ $(CH_2)_cNR^{15}SO_2(CH_2)_d(CH_2CH_2O)_eR^{23}$, —$(CH_2)_a$ $(CH_2CH_2O)_b(CH_2)_cSO_2NR^{16}(CH_2)_d(CH_2CH_2O)_e$ $R^{24}$, —$(CH2)_a(CH_2CH_2O)_b(CH_2)_cNR^{17}CO(CH_2)_d$ $(CH_2CH_2O)_eR^{25}$, —$(CH2)_a(CH_2CH_2O)_b(CH_2)_c$ $NR^{18}CO_2(CH_2)_d(CH_2CH_2O)_eR^{26}$, or —$(CH_2)_a$ $(CH_2CH_2O)_b(CH_2)_cOC(O)NR^{19}CO_2(CH_2)_d$ $(CH_2CH_2O)_eR^{27}$; —$(CH_2)_cOR^{68}$, —$CH_2(CHOH)_c$ $R^{69}$, —$CH_2(CHOH)_cCO_2H$, —$(CHCO_2H)_cCO_2H$, —$(CH_2)_cNR^{70}R^{71}$, —$CH[(CH_2)_fNH_2]_cCO_2H$, —$CH[(CH_2)_fNH_2]_cCH_2OH$, —$CH_2(CHNH_2)_c$ $CH2NR^{72}R^{73}$, —$(CH_2CH_2O)_eR^{74}$, —$(CH_2)_fCO$ $(CH_2CH_2O)_eR^{75}$, —$(CH_2)_u(CH_2CH_2O)_j(CH_2)_k$ $NR^{58}C(O)NR^{59}(CH_2)_l(CH_2CH_2O)_oR^{76}$, —$(CH_2)_u$ $(CH_2CH_2O)_j(CH_2)_kNR^{60}C(S)NR^{61}(CH_2)_l$ $(CH_2CH_2O)_oR^{77}$, —$(CH_2)_u(CH_2CH_2O)_j(CH_2)_kC$ $(O)NR^{62}(CH_2)_l(CH_2CH_2O)_oR^{78}$, —$(CH_2)_u$ $(CH_2CH_2O)_j(CH_2)_kS(O)_2NR^{63}(CH_2)_l(CH_2CH_2O)_o$ $R^{79}$, —$(CH_2)_u(CH_2CH_2O)_j(CH_2)_kNR^{64}S(O)_2(CH_2)_l$ $(CH_2CH_2O)_oR^{80}$, —$(CH_2)_u(CH_2CH_2O)_j(CH_2)_k$ $NR^{65}C(O)(CH_2)_l(CH_2CH_2O)_oR^{81}$, —$(CH_2)_u$ $(CH_2CH_2O)_j(CH_2)_kNR^{66}C(O)O(CH_2)_l(CH_2CH_2O)_o$ $R^{82}$, or —$(CH_2)_u(CH_2CH_2O)_j(CH_2)_kOC(O)NR^{67}$ $(CH_2)_l(CH_2CH_2O)OR^{83}$, —$(CH_2)_aSO_3H$, —$(CH_2)_a$ $SO_3^-$, —$(CH_2)_aOSO_3H$, —$(CH_2)_aOSO_3^-$, —$(CH_2)_a$ $NHSO_3H$, —$(CH_2)_aNHSO_3^-$, —$(CH_2)_aPO_3H_2$, —$(CH_2)_aPO_3H^-$, —$(CH_2)_aPO_3^=$, —$(CH_2)_a$ $OPO_3H_2$, —$(CH_2)_aOPO_3H^-$, or —$(CH_2)_aOPO^{3-}$;
each of $R^2$, $R^{10}$, $R^{11}$, $R^{12}$, $R^{13}$, $R^{14}$, $R^{15}$, $R^{16}$, $R^{17}$, $R^{18}$, $R^{19}$, $R^{58}$, $R^{59}$, $R^{60}$, $R^{61}$, $R^{62}$, $R^{63}$, $R^{64}$, $R^{65}$, $R^{66}$ and $R^{67}$ is independently —H or —$CH_3$;
each of $R^{20}$, $R^{21}$, $R^{22}$, $R^{23}$, $R^{24}$, $R^{25}$, $R^{26}$, and $R^{27}$ is independently —H, —$CH_3$, —$(CH_2)_fNR^{28}C(O)$ $NR^{29}(CH_2)_g(CH_2CH_2O)_hR^{38}$, —$(CH_2)_f$ $NR^{30}CSNR^{31}(CH_2)_g(CH_2CH_2O)_hR^{39}$, —$(CH_2)_fC$ $(O)NR^{32}(CH_2)_g(CH_2CH_2O)_hR^{40}$, —$(CH_2)_fS(O)_2$ $NR^{33}(CH_2)_g(CH_2CH_2O)_hR^{41}$, —$(CH_2)_fNR^{34}S(O)_2$ $(CH_2)_g(CH_2CH_2O)_hR^{42}$, —$(CH_2)_fNR^{35}C(O)(CH_2)_g$ $(CH_2CH_2O)_hR^{43}$, —$(CH_2)_fNR^{36}C(O)O(CH_2)_g$ $(CH_2CH_2O)_hR^{44}$, —$(CH_2)_fOC(O)NR^{37}(CH_2)_g$ $(CH_2CH_2O)_hR^{45}$, —CO(AA), or —CONH(PS);
each of $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ is independently —H or —$CH_3$; each of $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, and $R^{80}$ is independently —H, —$CH_3$, —$(CH_2)_pS$ $(O)_2NR^{84}(CH_2)_q(CH_2CH_2O)_sR^{81}$, —$(CH_2)_pNR^{85}S$ $(O)_2(CH_2)_q(CH_2CH_2O)_sR^{83}$, —$(CH_2)_pNR^{86}C(O)$ $(CH_2)_q(CH_2CH_2O)_sR^{85}$, —$(CH_2)_pNR^{86}C(O)O$ $(CH_2)_q(CH_2CH_2O)_sR^{87}$, or —$(CH_2)_pOC(O)NR^{88}$ $(CH_2)_q(CH_2CH_2O)_sR^{89}$;
each of $R^{81}$, $R^{82}$, $R^{83}$, $R^{84}$, $R^{85}$, $R^{86}$, $R^{87}$, $R^{88}$, and $R^{89}$ is independently —H or —$CH_3$;
each (AA) is independently a polypeptide chain that includes one or more natural or unnatural α-amino acids linked together by peptide bonds;
each (PS) is independently a sulfated or non-sulfated polysaccharide chain comprising one or more monosaccharide units connected by glycosidic linkages;
each of t and u is independently 1, 2, 3, 4, or 5;
each of a, d, g, l, and q is independently 0, 1, 2, 3, 4, 5, 6, 7, 8, 9 or 10;
each of c, f, k, and p is independently 0, 1, 2, 3, 4, 5, 6, 7, 8, 9 or 10; and each of b, j, e, h, o, and s is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100,
wherein each NHR moiety optionally comprises a protecting group.

* * * * *

UNITED STATES PATENT AND TRADEMARK OFFICE
CERTIFICATE OF CORRECTION

| | |
|---|---|
| PATENT NO. | : 11,708,336 B2 |
| APPLICATION NO. | : 17/066702 |
| DATED | : July 25, 2023 |
| INVENTOR(S) | : Thomas E. Rogers |

It is certified that error appears in the above-identified patent and that said Letters Patent is hereby corrected as shown below:

In the Claims

Column 26, Claim 7, Line 50, delete "R2,".

Signed and Sealed this
Tenth Day of December, 2024

Katherine Kelly Vidal
*Director of the United States Patent and Trademark Office*